United States Patent
Guenther

(12) 
(10) Patent No.: US 6,730,821 B2
(45) Date of Patent: May 4, 2004

(54) TRANSGENIC MICE CONTAINING RETINA-SPECIFIC NUCLEAR RECEPTOR GENE DISRUPTIONS

(75) Inventor: Catherine Guenther, San Carlos, CA (US)

(73) Assignee: Deltagen, Inc., San Carlos, CA (US)

( * ) Notice: Subject to any disclaimer, the term of this patent is extended or adjusted under 35 U.S.C. 154(b) by 0 days.

(21) Appl. No.: 09/811,361

(22) Filed: Mar. 16, 2001

(65) Prior Publication Data

US 2004/0040046 A1 Feb. 26, 2004

Related U.S. Application Data

(60) Provisional application No. 60/190,348, filed on Mar. 16, 2000.

(51) Int. Cl.[7] .............. A01K 67/027; C12N 15/00; C12N 5/00; C12N 5/06; A01N 1/02
(52) U.S. Cl. .............. 800/18; 800/25; 435/325; 435/352; 435/354; 435/1.1
(58) Field of Search .................. 800/3, 18, 25; 435/1.1, 325, 352, 354

(56) References Cited

PUBLICATIONS

Chen et al., Retina–specific nuclear receptor: A potential regulator of cellular retinaldehyde–binding protein expressed in retinal pigment epithelium and muller glial cells, 1999, PNAS, vol. 96, pp. 15149–15154.*

Osterrieder et al., Lessons from gene knockouts, 1998, Rev. Sci. Tech. Off. Int. Epiz., vol. 17, pp. 351–364.*

Mansour et al., Disruption of the proto–oncogene int–2 in mouse embryo–derived stem cells: a general strategy for targeting mutations to non–selectable genes, 1988, Nature, vol. 336, pp. 348–352.*

Sigmund, Viewpoint: Are studies in genetically altered mice out of control?, 2000, Arterioscler Thromb. Vasc. Biol., vol. 20, pp. 1425–1429.*

Wall, Transgenic livestock: Progress and prospects for the future, 1996, Theriogenology, vol. 45, pp. 57–68.*

Akhmedov, N.B. et al., *PNAS*, 97(10):5551–5556, (2000), "A deletion in a photoreceptor–specific . . . ".

Chen, F. et al., *PNAS*, 96(26):15149–15154 (1999), "Retina–specific nuclear receptor: A potential . . . ".

Evans, *Science*, 240:889–895 (1988), "The Steroid and Thyroid Hormone Receptor Superfamily".

Forman, B. M. et al., *New Biologist*, 2(7):587–594 (1990), "Dimerization Among Nuclear Hormone . . . ,".

Liao, S. et al., *J. steroid Biochem.*, 34(1–6):41–51 (1989), "Androgen Receptors: Structures, . . . ".

* cited by examiner

*Primary Examiner*—Anne-Marie Falk
*Assistant Examiner*—Celine Qian
(74) *Attorney, Agent, or Firm*—Robert J. Driscoll

(57) ABSTRACT

The present invention relates to transgenic animals, as well as compositions and methods relating to the characterization of gene function. Specifically, the present invention provides transgenic mice comprising disruptions in genes, which are useful as models for disease and for identifying agents that modulate gene expression and gene function, and as potential treatments for various disease states and disease conditions.

6 Claims, 11 Drawing Sheets

FIGURE 2B pDG2:
GTTAACTACGTCAGGTGGCACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAAGATCCTTGAGAGTTTTCGCC
CCGAAGAACGTTCTCCAATGATGAGCACTTTTAAAGTTTCTGCTATGTGGCGCGGTATTATCCCGTGTTGACGCCGGGCAA
GAGCAACTCGGTCGCCGCATACACTATTCTCAGAATGACTTGGTTGAGTACTCACCAGTCACAGAAAAGCATCTTACGGA
TGGCATGACAGTAAGAGAATTATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCCTTGATCGTTGGGAACCGGAG
CTGAATGAAGCCATACCAAACGACGAGCGTGACACCACGATGCCTGTAGCAATGGCAACAACGTTGCGCAAACTATTAAC
TGGCGAACTACTTACTCTAGCTTCCCGGCAACAATTAATAGACTGGATGGAGGCGGATAAAGTTGCAGGACCACTTCTGC
GCTCGGCCCTTCCGGCTGGCTGGTTTATTGCTGATAAATCTGGAGCCGGTGAGCGTGGGTCTCGCGGTATCATTGCAGCA
CTGGGGCCAGATGGTAAGCCCTCCCGTATCGTAGTTTATCTACACGACGGGGAGTCAGGCAACTATGGATGAACGAAATAG
ACAGATCGCTGAGATAGGTGCCTCACTGATTAAGCATTGGTAACTGTCAGACCAAGTTTACTCATATATACTTTAGATTG
ATTTACCCCGGTTGATAATCAGAAAAGCCCCAAAAACAGGAAGATTGTATAAGCAAATATTTAAATTGTAAACGTTAATA
TTTTGTTAAAATTCGCGTTAAATTTTTGTTAAATCAGCTCATTTTTTAACCAATAGGCCGAAATCGGCAAAATCCCTTAT
AAATCAAAAGAATAGCCCGAGATAGGGTTGAGTGTTGTTCCAGTTTGGAACAAGAGTCCACTATTAAAGAACGTGGACTC
CAACGTCAAAGGGCGAAAAACCGTCTATCAGGGCGATGGCCCACTACGTGAACCATCACCCAAATCAAGTTTTTTGGGGT
CGAGGTGCCGTAAAGCACTAAATCGGAACCCTAAAGGGAGCCCCCGATTTAGAGCTTGACGGGGAAAGCGAACGTGGCGA
GAAAGGAAGGGAAGAAAGCGAAAGGAGCGGGCGCTAGGGCGCTGGCAAGTGTAGCGGTCACGCTGCGCGTAACCACCACA
CCCGCCGCGCTTAATGCGCCGCTACAGGGCGCGTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGATCTTCTTGAGATCCTTTTTTT
CTGCGCGTAATCTGCTGCTTGCAAACAAAAAAACCACCGCTACCAGCGGTGGTTTGTTGCCGGATCAAGAGCTACCAAC
TCTTTTTCCGAAGGTAACTGGCTTCAGCAGAGCGCAGATACCAAATACTGTTCTTCTAGTGTAGCCGTAGTTAGGCCACC
ACTTCAAGAACTCTGTAGCACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGATGCTCGTCAGGGGGGCG
GAGCCTATGGAAAAACGCCAGCAACGCGGCCTTTTTACGGTTCCTGGCCTTTTGCTGGCCTTTTGCTCACATGTAATGTG
AGTTAGCTCACTCATTAGGCACCCCAGGCTTTACACTTTATGCTTCCGGCTCGTATGTTGTGTGGAATTGTGAGCGGATA
ACAATTTCACACAGGAAACAGCTATGACCATGATTACGCCAAGCTACGTAATACGACTCACTAGGCGGCCGCGTTTAAAC
AATGTGCTCCTCTTTGGCTTGCTTCCGCGGGCCAAGCCAGACAAGAACCAGTTGACGTCAAGCTTCCCGGGACGCGTGCT
AGCGGCGCGCCGAATTCCTGCAGGATTCGAGGGCCCCTGCAGGTCAATTCTACCGGGTAGGGGAGGCGCTTTTCCCAAGG
CAGTCTGGAGCATGCGCTTTAGCAGCCCCGCTGGCACTTGGCGCTACACAAGTGGCCTCTGGCCTCGCACACATTCCACA
TCCACCGGTAGCGCCAACCGGCTCCGTTCTTTGTGGCCCCTTCGCGCCACCTTCTACTCCTCCCCTAGTCAGGAAGTTC
CCCCCCGCCCCGCAGCTCGCGTCGTGCAGGACGTGACAAATGGAAGTAGCACGTCTCACTAGTCTCGTGCAGATGGACAG
CACCGCTGAGCAATGGAAGCGGGTAGGCCTTTGGGGCAGCGGCCAATAGCAGCTTTGCTCCTTCGCTTTCTGGGCTCAGA
GGCTGGGAAGGGCTGGGTCCGGGGGCGGGCTCAGGGGCGGGCTCAGGGGCGGGGCCGGCGCGAAGGTCCTCCCGAGGCCC
GGCATTCTCGCACGCTTCAAAAGGCACGTCTGCCGCGCTGTTCTCCTCTTCCTCATCTCCGGGCCTTTCGACCTGCAGC
CAATATGGGATCGGCCATTGAACAAGATGGATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTGTCAGCGCAGGGGCGCCCGGTTCTTTTTGTC
AAGACCGACCTGTCCGGTGCCCTGAATGAACTGCAGGACGAGGCAGCGCGGCTATCGTGGCTGGCCACGACGGGCGTTCC
TTGCGCAGCTGTGCTCGACGTTGTCACTGAAGCGGGAAGGGACTGGCTGCTATTGGGCGAAGTGCCGGGGCAGGATCTCC
TGTCATCTCACCTTGCTCCTGCCGAGAAAGTATCCATCATGCCTGATGCAATGCGGCGGCTGCATACGCTTGATCCGGCT
ACCTGCCCATTCGACCACCAAGCGAAACATCGCATCGAGCGAGCACGTACTCGGATGGAAGCCGGTCTTGTCGATCAGGA
TGATCTGGACGAAGAGCATCAGGGGCTCGCGCCAGCCGAACTGTTCGCCAGGCTCAAGGCGCGCATGCCCGACGGCGATG
ATCTCGTCGTGACCCATGGCGATGCCTGCTTGCCGAATATCATGGTGGAAAATGGCCGCTTTTCTGGATTCATCGACTGT
GGCCGGCTGGGTGTGGCGGACCGCTATCAGGACATAGCGTTGGCTACCCGTGATATTGCTGAAGAGCTTGGCGGCGAATG
GGCTGACCGCTTCCTCGTGCTTTACGGTATCGCCGCTCCCGATTCGCAGCGCATCGCCTTCTATCGCCTTCTTGACGAGT
TCTTCTGAGGGGATCGATCCGTCCTGTAAGTCTGCAGAAATTGATGATCTATTAAACAATAAAGATGTCCACTAAAATGG
AAGTTTTTCCTGTCATACTTTGTTAAGAAGGGTGAACAGAGTACCTACATTTTGAATGGAAGGATTGGAGCTACGGGG
GTGGGGGTGGGGTGGGATTAGATAAATGCCTGCTCTTTACTGAAGGCTCTTTACTATTGCTTTATGATAATGTTTCATAG
TTGGATATCATAATTTAAACAAGCAAAACCAAATTAAGGGCCAGCTCATTCCTCCCACTCATGATCTATAGATCTATAGA
TCTCTCCTGGGATCATTGTTTTTCTCTTGATTCCCACTTTGTGGTTCTAAGTACTGTGGTTTCCAAATGTGTCAGTTTCA
TAGCCTGAAGAACGAGATCAGCAGCCTCTGTTCCACATACACTTCATTCTCAGTATTGTTTTGCCAAGTTCTAATTCCAT
CAGAAGCTGACTCTAGATCTGGATCCGGCCAGCTAGGCCGTCGACCTCGAGTGATCAGGTACCAAGGTCCTCGCTCTGTG
TCCGTTGAGCTCGACGACACAGGACACGCAAATTAATTAAGGCCGGCCCGTACCCTCTAGTCAAGGCCTTAAGTGAGTCG
TATTACGACTGGCCGTCGTTTTACAACGTCGTGACTGGGAAAAACCCTGGCGTTACCCAACTTAATCGCCTTGCAGCACA
TCCCCCTTTCGCCAGCTGGCGTAATAGCGAAGAGGCCCGCACCGATCGCCCTTCCCAACAGTTGCGCAGCCTGAATGGCG
AATGGCGCTTTGCCTTGGTAATAAAGCCCGCTTCGGCGGGCTTTTTTTT

FIGURE 3B pDG4:
GTTTAATAGTAATCAATTACGGGGTCATTAGTTCATAGCCCATATATGGAGTTCCGCGTTACATAACTTACGGTAAATGG
CCCGCCTGGCTGACCGCCCAACGACCCCCGCCCATTGACGTCAATAATGACGTATGTTCCCATAGTAACGCCAATAGGGA
CTTTCCAATGACGTCAATGGGTGGAGTATTTACGGTAAACTGCCCACTTGGCAGTACATCAAGTGTATCATATGCCAAGT
ACGGCCCCCTATTGACGTCAATGACGGAAAATGGCCCGCCTGGCATTAAGCCCAGTACATGACCTTATGGGACTTTCCTAC
TTGGCAGTACATCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAAATCAACGGGAC
TTTCCAAAATGTCGTAACAACTCCGCCCCATTGACGCAAATGGGCGGTAGGCGTGTACGGTGGGAGGTCTATATAAGCAG
AGCTGGTTTAGTGAACCGTCAGATCCGCTAGCGCTACCGGTCGCCACCATGGTGAGCAAGGGCGAGGAGCTGTTCACCGG
GGTGGTGCCCATCCTGGTCGAGCTGGACGGCGACGTAAACGGCCACAAGTTCAGCGTGTCCGGCGAGGGCGAGGGCGATG
CCACCTACGGCAAGCTGACCCTGAAGTTCATCTGCACCACCGGCAAGCTGCCCGTGCCCTGGCCCACCCTCGTGACCACC
CTGACCTACGGCGTGCAGTGCTTCAGCCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCCTGGGGCACAAGCTGGAGTAC
AACTACAACAGCCACAACGTCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGGTCCTGCTGGAGTTC
GTGACCGCCGCCGGGATCACTCTCGGCATGGACGAGCTGTACAAGTCCGGACTCAGATCCACCGGATCTAGATAACTGAT
CATAATCAGCCATACCACATTTGTAGAGGTTTTACTTGCTTTAAAAAACCTCCCACACCTCCCCCTGAACCTGAAACATA
AAATGAATGCAATTGTTGTTGTTAACTTGTTTATTGCAGCTTATAATGGTTACAAATAAAGCAATAGCATCACAAATTTC
ACAAATAAAGCATTTTTTTCACTGCATTCTAGTTGTGGTTTGTCCAAACTCATCAATGTATCTTAACGCGAACTACGTCA
GGTGGCACTTTTCGGGGAAATGTGCGCGGAACCCCTATTTGTTTATTTTTCTAAATACATTCAAATATGTATCCGCTCAT
GAGACAATAACCCTGATAAATGCTTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAAGTAAAAGATGCTGAAGATCAG
TTGGGTGCACGAGTGGGTTACATCGAACTGGATCTCAACAGCGGTAAGATCCTTGAGAGTTTTCGCCCCGAAGAACGTTC
TCCAATGATGAGCACTTTTAAAGTTCTGCTATGTGGCGCGGTATTATCCCGTGTTGACGCCGGGCAAGAGCAACTCGGTC
GCCGCATACACTATTCTCAGAATGACTTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAACCGGAGCTGAATGAAGCCA
TACCAAACGACGAGCGTGACACCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTAGATTGATTTACCCCGGTT
GATAATCAGAAAAGCCCCAAAAACAGGAAGATTGTATAAGCAAATATTTAAATTGTAAACGTTAATAATTTGTTAAAATT
CGCGTTAAATTTTTGTTAAATCAGCTCATTTTTTAACCAATAGGCCGAAATCGGCAAAATCCCTTATAAATCAAAAGAAT
AGCCCGAGATAGGGTTGAGTGTTGTTCCAGTTTGGAACAAGAGTCCACTATTAAAGAACGTGGACTCCAACGTCAAAGGG
CGAAAAACCGTCTATCAGGGCGATGGCCCACTACGTGAACCATCACCCAAATCAAGTTTTTTGGGGTCGAGGTGCCGTAA
AGCACTAAATCGGAACCCTAAAGGGAGCCCCCGATTTAGAGCTTGACGGGGAAAGCGAACGTGGCGAGAAAGGAAGGGAA
GAAAGCGAAAGGAGCGGGCGCTAGGGCGCTGGCAAGTGTAGCGGTCACGCTGCGCGTAACCACCACACCCGCCGCGCTTA
ATGCGCCGCTACAGGGCGCGTAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCCTTTTTTTCTGCGCGTAATCT
GGTGCTTGCAAACAAAAAAACCACCGCTACCAGCGGTGGTTTGTTTGCCGGATCAAGAGCTACCAACTCTTTTTCCGAAG
GTAACTGGCTTCAGCAGAGCGCAGATACCAAATACTGTTCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTTCGTGCACACAGCCCAGCTTG
GAGCGAACGACCTACACCGAACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAGGGGGAAACGCCTGGTATCTTT
ATAGTCCTGTCGGGTTTCGCCACCTCTGACTTGAGCGTCGATTTTTGTGATGCTCGTCAGGGGGGCGGAGCCTATGGAAA
AACGCCAGCAACGCGGCCTTTTTACGGTTCCTGGCCTTTTGCTGGCCTTTTGCTCACATGTAATGTGAGTTAGCTCACTC
ATTAGGCACCCCAGGCTTTACACTTTATGCTTCCGGCTCGTATGTTGTGTGGAATTGTGAGCGGATAACAATTTCACACA
GGAAACAGCTATGACCATGATTACGCCAAGCTACGTAATACGACTCACTAGGCGGCCGCGTTTAAACAATGTGCTCCTCT
TTGGCTTGCTTCCGCGGGCAAGCCAGACAAGAACCAGTTGACGTCAAGCTTCCCGGGACGCGTGCTAGCGGCGCGCCGA
ATTCCTGCAGGATTCGAGGGCCCCTGCAGGTCAATTCTACCGGGTAGGGGAGGCGCTTTTCCCAAGGCAGTCTGGAGCAT
GCGCTTTAGCAGCCCCGCTGGCACTTGGCGCTACACAAGTGGCCTCTGGCCTCGCACACATTCCACATCCACCGGTAGCG
CCAACCGGCTCCGTTCTTTGGTGGCCCCTTCGCGCCACCTTCTACTCCTCCCCTAGTCAGGAAGTTCCCCCCCGCCCCGC
AGCTCGCGTCGTGCAGGACGTGACAAATGGAAGTAGCACGTCTCACTAGTCTCGTGCAGATGGACAGCACCGCTGAGCAA
TGGAAGCGGGTAGGCCTTTGGGGCAGCGGCCAATAGCAGCTTTGCTCCTTCGCTTTCTGGGCTCAGAGGCTGGGAAGGGG
TGGGTCCGGGGGCGGGCTCAGGGGCGGGCTCAGGGGCGGGGCGGGCGCGAAGGTCCTCCCGAGGCCCGGCATTCTCGCAC
GCTTCAAAAGCGCACGTCTGCCGCGCTGTTCTCCTCTTCCTCATCTCCGGGCCTTTCGACCTGCAGCCAATATGGGATCG
GCCATTGAACAAGATGGATTGCACGCAGGTTCTCCGGCCGCTTGGGTGGAGAGGCTATTCGGCTATGACTGGGCACAACA
GACAATCGGCTGCTCTGATGCCGCCGTGTTCCGGCTGTCAGCGCAGGGGCGCCCGGTTCTTTTTGTCAAGACCGACCTGT
CCGGTGCCCTGAATGAACTGCAGGACGAGGCAGCGCGGCTATCGTGGCTGGCCACGACGGGCGTTCCTTGCGCAGCTGTG
CTCGACGTTGTCACTGAAGCGGGAAGGGACTGGCTGCTATTGGGCGAAGTGCCGGGGCAGGATCTCCTGTCATCTCACCT

```
TGCTCCTGCCGAGAAAGTATCCATCATGGCTGATGCAATGCGGCGGCTGCATACGCTTGATCCGGCTACCTGCCCATTCG
ACCACCAAGCGAAACATCGCATCGAGCGAGCACGTACTCGGATGGAAGCCGGTCTTGTCGATCAGGATGATCTGGACGAA
GAGCATCAGGGGCTCGCGCCAGCCGAACTGTTCGCCAGGCTCAAGGCGCGCATGCCCGACGGCGATGATCTCGTCGTGAC
CCATGGCGATGCCTGCTTGCCGAATATCATGGTGGAAAATGGCCGCTTTTCTGGATTCATCGACTGTGGCCGGCTGGGTG
TGGCGGACCGCTATCAGGACATAGCGTTGGCTACCCGTGATATTGCTGAAGAGCTTGGCGGCGAATGGGCTGACCGCTTC
CTCGTGCTTTACGGTATCGCCGCTCCCGATTCGCAGCGCATCGCCTTCTATCGCCTTCTTGACGAGTTCTTCTGAGGGGA
TCGATCCGTCCTGTAAGTCTGCAGAAATTGATGATCTATTAAACAATAAAGATGTCCACTAAAATGGAAGTTTTTCCTGT
CATACTTTGTTAAGAAGGGTGAGAACAGAGTACCTACATTTTGAATGGAAGGATTGGAGCTACGGGGTGGGGGTGGGGT
GGGATTAGATAAATGCCTGCTCTTTACTGAAGGCTCTTTACTATTGCTTTATGATAATGTTTCATAGTTGGATATCATAA
TTTAAACAAGCAAAACCAAATTAAGGGCCAGCTCATTCCTCCCACTCATGATCTATAGATCTATAGATCTCTCGTGGGAT
CATTGTTTTTCTCTTGATTCCCACTTTGTGGTTCTAAGTACTGTGGTTTCCAAATGTGTCAGTTTCATAGCCTGAAGAAC
GAGATCAGCAGCCTCTGTTCCACATACACTTCATTCTCAGTATTGTTTTGCCAAGTTCTAATTCCATCAGAAGCTGACTC
TAGATCTGGATCCGGCCAGCTAGGCCGTCGACCTCGAGTGATCAGGTACCAAGGTCCTCGCTCTGTGTCCGTTGAGCTCG
ACGACACAGGACACGCAAATTAATTAAGGCCGGCCCGTACCCTCTAGTCAAGGCCTTAAGTGAGTCGTATTACGGACTGG
CCGTCGTTTTACAACGTCGTGACTGGGAAAACCCTGGCGTTACCCAACTTAATCGCCTTGCAGCACATCCCCCTTTCGCC
AGCTGGCGTAATAGCGAAGAGGCCCGCACCGATCGCCCTTCCCAACAGTTGCGCAGCCTGAATGGCGAATGGCGCTTCGC
TTGGTAATAAAGCCCGCTTCGGCGGGCTTTTTTTT
```

FIGURE 3B (Continued)

| Annealing site | Sequence | | Sequence after digestion | |
|---|---|---|---|---|
| 1 | 5' tgtgctcctcttggcttgcttccaa... 3'<br>3' acacgaggagaaaccgaacgaaggtt... 5' | | 5' tgtgctcctcttggcttgcttccaa... 3'<br>3' tt... 5' | |
| 2 | 5' ctggttcttgtctggcttggcccaa... 3'<br>3' gaccaagaacagaccgaaccgggtt... 5' | | 5' ctggttcttgtctggcttggcccaa... 3'<br>3' tt... 5' | |
| 3 | 5' ggtcctcgctctgtgtccgttgaa... 3'<br>3' ccaggagcgagacacaggcaactt... 5' | | 5' ggtcctcgctctgtgtccgttgaa... 3'<br>3' tt... 5' | |
| 4 | 5' tttgcgtgtcctgtgtcgtcgaa... 3'<br>3' aaacgcacaggacacagcagctt... 5' | | 5' tttgcgtgtcctgtgtcgtcgaa... 3'<br>3' tt... 5' | |

FIGURE 4

| Annealing site | Sequence | | Sequence after digestion | |
|---|---|---|---|---|
| 1 | 5'<br>3' | AAtgtgctcctctttggcttgcttCCGC<br>Ttacacgaggagaaaccgaacgaagg | 5'<br>3' | AA<br>Ttacacgaggagaaaccgaacgaagg | 3'<br>5' |
| 2 | 5'<br>3' | AActggttcttgtctggcttggCCCGC<br>Ttgaccaagaacagaccgaacccggg | 5'<br>3' | AA<br>Ttgaccaagaacagaccgaacccggg | 3'<br>5' |
| 3 | 5'<br>3' | AAggtcctcgtctgtgtccgttGAGCT<br>Ttccaggagcgagacacaggcaac | 5'<br>3' | AA<br>Ttccaggagcgagacacaggcaac | 3'<br>5' |
| 4 | 5'<br>3' | AAtttgcgtgtcctgtgtcgtcGAGCT<br>Ttaaacgcacaggacacagcagc | 5'<br>3' | AA<br>Ttaaacgcacaggacacagcagc | 3'<br>5' |

FIGURE 5

```
TCGGTTGGGCCCAGCAACTTCTAGCAAGCAGGCTACCCTTAGGACCATCCATATCCGATGAGCTCTACAG
TGGCTGCCTCCACTATGCCTGTGTCTGTGGCGGCCTCCAAGAAGGAGTCTCCAGGTAGATGGGCCTTGG
AGAGGATCCAACAGGTGTGGGCCCCTCGCTCCAGTGCCGAGTGTGTGGGGACAGCAGCAGTGGGAAACAT
TATGGCATCTATGCCTGCAATGGCTGCAGTGGCTTCTTCAAGAGGAGTGTGAGAAGGAGGCTCATCTACA
GGTGCCAAGTCGGGCAGGGATGTGCCCAGTGGATAAGGCCCATCGCAATCAGTGCCAGGCCTGCCGGCT
GAAGAAGTGCTTACAAGCAGGCATGAACCAAGATGCTGTGCAGAATGAGCGCCAACCTCGGAGCATGGCT
CAGGTCCACCTGGATGCCATGGAAACAGGCAGTGACCCCGATCAGAACCAGTGGTAGCCTCTCCTGCTC
TGGCAGGGCCCAGTCCCCGGGGCCCCACGTCTGTGTCTGCAACCAGAGCCATGGGCCACCACTTTATGGC
CAGCCTTATCACCGCCGAAACTTGTGCTAAACTGGAGCCAGAGGACGCTGAAGAGAATATTGATGTCACC
AGCAATGACCCCGAGTTCCCCGCATCCCCCTGCAGTCTGGATGGCATCCATGAGACATCTGCTCGCCTGC
TCTTCATGGCTGTCAAATGGGCCAAAAACTTGCCTGTGTTTTCCAACCTGCCTTTCCGGGACCAGGTGAT
CTTGCTGGAAGAGGCATGGAATGAGCTTTTCCTTCTTGGAGCCATACAGTGGTCTCTGCCCCTGGACAGC
TGCCCACTGCTGGCACCACCTGAGGCGTCCGGCAGCTCTCAGGGCAGGCTGGCCTTGGCCAGTGCAGAGA
CGCGCTTCCTGCAGGAAACCATCTCCCGGTTCCGAGCTCTGGCAGTGGATCCCACAGAGTTTGCCTGCCT
GAAGGCCCTGGTCCTCTTCAAACCTGAAACACGAGGCCTGAAGGATCCTGAGCACGTGGAGGCTTTGCAG
GACCAGTCCCAGGTGATGCTAAGCCAGCATAGCAAGGCTCACCACCCCAGCCAGCCTGTGAGGTTTGGGA
AATTGCTCCTCCTGCTCCCATCTTTGAGGTTCCTCACGGCTGAGCGCATTGAGCTTCTCTTCTTCAGAAA
GACCATAGGGAACACTCCGATGGAGAAGCTCCTGTGTGACATGTTCAAAAACTAGTTGGGAGTGCCAAGT
GTCCACAGGCACCCAGGGGGGCAGCACATCTTAGAAGCTAAATAGTTCCCTGCCTTTCTCAGCCAGTAAT
TCCACATTCAGGTATTCCTACCTAGCAGAAATTTCTCCCAAAATATATTATTGGCATATTCATTGCCATC
CTAATCTTAATACCCCTAACTCTGCTTGGGCAGTAGAATGCATGGATGCGTTGTTATATTCATAGGAGAA
ACAGCTTTGGCAAAAAAAAAAAAAAAAAAAAAAAAAAAAAAAAAAAAAAAAAAAAAAAAAAAAAAAAAAA
(SEQ ID NO:19 )
```

Targeting Vector (5' arm; 200 bp flanking neo insert):

```
AGACTGAAAGACAGACAGACAGACAGACAGGGGTTAAAGATGGATGCATCGGTTGGGCCCAGCAACT
TCTAGCAAGCAGGCTACCCTTAGGACCATCCATATCCGATGAGCTCTACAGTGGCTGCCTCCACTATG
CCTGTGTCTGTGGCGGCCTCCAAGAAGGAGTCTCCAGGTAGATGGGGCCTTGGAGAGGATCCAAC
(SEQ ID NO: 20 )
```

Targeting Vector (3' arm; 200 bp flanking neo insert):

```
CTCCAGTGCCGAGTGTTTGGGGACAGCAGCAGTGGGAAACATTATGGCATCTATGCCTGCAATGGCTG
CAGTGGCTTCTTCAAGAGGAGTGTGAGAAGGAGGCTCATCTACAGGTGCCACAGCTCTGCCGGCCTG
CCCCGGTGTGCCTAGCACGGGTGGAGGGCGTTCAGGGAAAGCGGAAGACGAGACCAGGGCAAACA
(SEQ ID NO: 21 )
```

FIG. 8

… administering an effective amount of the agent to a transgenic animal, preferably a mouse, having a disruption in a retina-specific nuclear receptor gene. The method includes measuring a response of the transgenic animal, for example, to the agent, and comparing the response of the transgenic animal to a control mouse. The response of the transgenic animal as compared to the control mouse may serve as an indication of the specificity or activity of the agent. Compounds that may have an effect on retina-specific nuclear receptor gene expression or function may also be screened against cells in cell-based assays, for example, to identify such compounds.

The present invention also provides methods of identifying agents useful as therapeutic agents for treating conditions associated with a disruption in a retina-specific nuclear receptor gene. In a preferred embodiment, conditions include those associated with the phenotypes of the mice of the present invention. In accordance with this method, the present invention provides animal models useful in identifying compounds that are able to affect a phenotype, such as a physiological or behavioral phenotype associated with a disruption of a retina-specific nuclear receptor gene. The method involves, for example, administering a putative agent to a transgenic animal. The response of the transgenic animal to the putative agent is then measured and compared to the response of a "normal" or wild-type mouse, or alternatively compared to a transgenic animal control (without agent administration). The invention further provides agents identified according to such methods.

The invention also provides cell lines comprising nucleic acid sequences encoding a retina-specific nuclear receptor. Such cell lines may be capable of expressing such sequences by virtue of operable linkage to a promoter functional in the cell line. Preferably, expression of the sequence encoding a retina-specific nuclear receptor is under the control of an inducible promoter. Also provided are methods of identifying agents that interact with retina-specific nuclear receptor, comprising the steps of contacting a retina-specific nuclear receptor with an agent and detecting an agent/retina-specific nuclear receptor complex. Such complexes can be detected by, for example, measuring expression of an operably linked detectable marker.

The invention further provides methods of treating diseases or conditions associated with a disruption in a gene encoding a retina-specific nuclear receptor, and more particularly, to a disruption in the expression or function of a retina-specific nuclear receptor. In a preferred embodiment, methods of the present invention involve treating diseases or conditions associated with a disruption in retina-specific nuclear receptor expression or function, including administering to a subject in need, a therapeutic agent which effects retina-specific nuclear receptor expression or function. In accordance with this embodiment, the method comprises administration of a therapeutically effective amount of a natural, synthetic, semi-synthetic, or recombinant retina-specific nuclear receptor or fragment thereof as well as natural, synthetic, semi-synthetic or recombinant analogs.

The present invention further provides methods of treating diseases or conditions associated with disrupted retina-specific nuclear receptor expression or function, wherein the methods comprise detecting and replacing through gene therapy mutated retina-specific nuclear receptor genes.

DEFINITIONS

As used herein, "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions, and preferably includes all sequences necessary for normal gene expression including promoters, enhancers and other regulatory sequences.

As used herein, "gene targeting" is a type of homologous recombination that occurs when a fragment of genomic DNA is introduced into a mammalian cell and that fragment locates and recombines with endogenous homologous sequences.

"Disruption" of a target gene occurs when a fragment of genomic DNA locates and recombines with an endogenous homologous sequence such that production of the normal wild type gene product is inhibited or functionally disrupted, resulting in, for example, partial or complete loss of expression of a protein encoded by a target gene. Non-limiting examples of disruption include insertion, missense, frame-shift and deletion mutations. Gene targeting can also alter a promoter, enhancer, or splice site of a target gene to cause disruption, and can also involve replacement of a promoter with an exogenous promoter such as an inducible promoter described below.

As used herein, a "transgenic animal" is an animal that contains within its genome a specific gene that has been disrupted or inactivated completely or partially by the method of gene targeting. The transgenic animal includes both the heterozygote animal (i.e., one defective allele and one wild-type allele) and the homozygous animal (i.e., two defective alleles).

The terms "polynucleotide" and "nucleic acid molecule" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules.

"Oligonucleotide" refers to polynucleotides of between 5 and about 100 nucleotides of single- or double-stranded DNA. Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

A "fragment" of a polynucleotide is a polynucleotide comprised of at least 9 contiguous nucleotides, preferably at least 15 contiguous nucleotides and more preferably at least 45 nucleotides, of coding or non-coding sequences.

As used herein, "base pair," also designated "bp," refers to the complementary nucleic acid molecules. In DNA there are four "types" of bases: the purine base adenine (A) is hydrogen bonded with the pyrimidine base thymine (T), and the purine base guanine (G) with the pyrimidine base cytosine (C). Each hydrogen bonded base pair set is also known as a Watson-Crick base-pair. A thousand base pairs is often called a kilobase pair, or kb. A "base pair mismatch" refers to a location in a nucleic acid molecule in which the bases are not complementary Watson-Crick pairs. The phrase "does not include at least one type of base at any position" refers to a nucleotide sequence which does not have one of the four bases at any position. For example, a sequence lacking one nucleotide (i.e., lacking one type of base) could be made up of A, G, T base pairs and contain no C residues.

As used herein, the term "construct" refers to an artificially assembled DNA segment to be transferred into a target tissue, cell line or animal, including human. Typically, the construct will include the gene or a sequence of particular interest, a marker gene and appropriate control sequences. The term "plasmid" refers to an autonomous, self-replicating extrachromosomal DNA molecule. In a preferred embodiment, the plasmid construct of the present invention contains a positive selection marker positioned between two flanking regions of the gene of interest. Optionally, the construct can also contain a screening marker, for example, green fluorescent protein (GFP). If present, the screening marker is positioned outside of and some distance away from the flanking regions.

The term "polymerase chain reaction" or "PCR" refers to a method of amplifying a DNA base sequence using a heat-stable polymerase such as Taq polymerase, and two oligonucleotide primers; one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce exponential and highly specific amplification of the desired sequence. PCR also can be used to detect the existence of the defined sequence in a DNA sample. "Long-range" refers to PCR conditions which allow amplification of large nucleotides stretches, for example, greater than 1 kb.

As used herein, the term "positive selection marker" refers to a gene encoding a product that enables only the cells that carry the gene to survive and/or grow under certain conditions. For example, plant and animal cells that express the introduced neormycin resistance (Neo$^r$) gene are resistant to the compound G418. Cells that do not carry the Neo$^r$ gene marker are killed by G418. Other positive selection markers will be known to those of skill in the art.

"Positive-negative selection" refers to the process of selecting cells that carry a DNA insert integrated at a specific targeted location (positive selection) and also selecting against cells that carry a DNA insert integrated at a non-targeted chromosomal site (negative selection). Non-limiting examples of negative selection inserts include the gene encoding thymidine kinase (tk). Genes suitable for positive-negative selection are known in the art, see e.g., U.S. Pat. No. 5,464,764.

"Screening marker" or "reporter gene" refers to a gene that encodes a product that can readily be assayed. For example, reporter genes can be used to determine whether a particular DNA construct has been successfully introduced into a cell, organ or tissue. Non-limiting examples of screening markers include genes encoding for green fluorescent protein (GFP) or genes encoding for a modified fluorescent protein. "Negative screening marker" is not to be construed as negative selection marker; a negative selection marker typically kills cells that express it.

The term, "vector" refers: to a DNA molecule that can carry inserted DNA and be perpetuated in a host cell. Vectors are also known as cloning vectors, cloning vehicles or vehicles. The term includes vectors that function primarily for insertion of a nucleic acid molecule into a cell, replication vectors that function primarily for the replication of nucleic acid, and expression vectors that function for transcription and/or translation of the DNA or RNA. Also included are vectors that provide more than one of the above functions. In a preferred embodiment, the vector contains sites useful in the methods described herein, for example, the vectors "pDG2" or "pDG4" as described herein.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs of the present invention.

The term "genomic library" refers to a collection of clones made from a set of randomly generated overlapping DNA fragments representing the genome of an organism. A "cDNA library" (complementary DNA library) is a collection of mRNA molecules present in a cell, tissue, or organism, turned into cDNA molecules with the enzyme reverse transcriptase, then inserted into vectors (other DNA molecules which can continue to replicate after addition of foreign DNA). Exemplary vectors for libraries include bacteriophage (also known as "phage"), which are viruses that infect bacteria, for example lambda phage. The library can then be probed for the specific cDNA (and thus mRNA) of interest. In one embodiment, library systems which combine the high efficiency of a phage vector system with the convenience of a plasmid system (for example, ZAP system from Stratagene, La Jolla, Calif.) are used in the practice of the present invention.

The term "homologous recombination" refers to the exchange of DNA fragments between two DNA molecules or chromatids at the site of homologous nucleotide sequences, i.e., those sequences preferably having at least about 70 percent sequence identity, typically at least to about 85 percent identity, and preferably at least about 90 percent identity. Homology can be determined using a "BLASTN" algorithm. It is understood that homologous sequences can accommodate insertions, deletions and substitutions in the nucleotide sequence. Thus, linear sequences of nucleotides can be essentially identical even if some of the nucleotide residues do not precisely correspond or align.

As used herein the term "ligation-independent cloning" is used in the conventional sense to refer to incorporation of a DNA molecule into a vector or chromosome without the use of kinases or ligases. Ligation-independent cloning techniques are described, for instance, in Aslanidis & de Jong, *Nucleic Acids Res.*, 18:6069–74 and U.S. patent application Ser. No. 07/847,298 (1991).

As used herein, the term "target sequence" (alternatively referred to as "target gene sequence" or "target DNA sequence") refers to the nucleic acid molecule with any polynucleotide having a sequence in the general population that is not associated with any disease or discernible phenotype. It is noted that in the general population, wild-type genes may include multiple prevalent versions that contain alterations in sequence relative to each other and yet do not cause a discernible pathological effect. These variations are designated "polymorphisms" or "allelic variations."

In a preferred embodiment, the target DNA sequence comprises a portion of a particular gene or genetic locus in the individual's genomic DNA. The target DNA sequence encodes a retina-specific nuclear receptor. According to one embodiment, the target DNA comprises part of a particular gene or genetic locus in which the function of the gene product is not known, for example, a gene identified using a partial cDNA sequence such as an EST. The target retina-specific nuclear receptor gene comprises the coding sequence represented by SEQ ID NO:21 or a naturally occurring allelic variation or homologue of the target gene.

The term "exonuclease" refers to an enzyme that cleaves nucleotides sequentially from the free ends of a linear nucleic acid substrate. Exonucleases can be specific for double or single-stranded nucleotides and/or directionally specific, for instance, 3'-5' and/or 5'-3'. Some exonucleases exhibit other enzymatic activities, for example, T4 DNA polymerase is both a polymerase and an active 3'-5' exonuclease. Other exemplary exonucleases include exonuclease III which removes nucleotides one at a time from the 5'-end of duplex DNA which does not have a phosphorylated 3'-end, exonuclease VI which makes oligonucleotides by cleaving nucleotides off of both ends of single-stranded DNA, and exonuclease lambda which removes nucleotides from the 5' end of duplex DNA which have 5'-phosphate groups attached to them.

The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. As used herein, the expression "enzyme-directed site-specific recombination" is intended to include the following three events:

1. deletion of a pre-selected DNA segment flanked by recombinase target sites;
2. inversion of the nucleotide sequence of a pre-selected DNA segment flanked by recombinase target sites; and
3. reciprocal exchange of DNA segments proximate to recombinase target sites located on different DNA molecules.

BRIEF DESCRIPTION OF THE DRAWINGS

FIG. 4 (SEQ ID NO:3 through SEQ ID NO:10) shows the nucleic acid sequence before and after T4 DNA polymerase treatment of annealing sites 1–4 contained on the ends of PCR-amplified genomic DNA.

FIG. 5 (SEQ ID NO:11 through SEQ ID NO:18) shows the nucleic acid sequence before and after T4 DNA polymerase treatment of annealing site 1–4 contained within the pDG2 vector.

FIG. 8 shows the polynucleotide sequence identified as SEQ ID NO:19. FIG. 8 also shows the sequences identified as SEQ ID NO:20 and SEQ ID NO:21, which were used in the retina-specific nuclear receptor gene targeting construct.

DETAILED DESCRIPTION OF THE INVENTION

The invention is based, in part, on the evaluation of the expression and role of genes and gene expression products, primarily those associated with retina-specific nuclear receptor. Among others, the invention permits the definition of disease pathways and the identification of diagnostically and therapeutically useful targets. For example, genes which are mutated or down-regulated under disease conditions may be involved in causing or exacerbating the disease condition. Treatments directed at up-regulating the activity of such genes or treatments which involve alternate pathways, may ameliorate the disease condition.

Any technique known in the art may be used to introduce a target gene transgene into animals to produce the founder lines of transgenic animals. Such techniques include, but are not limited to pronuclear microinjection (U.S. Pat. No. 4,873,191); retrovirus mediated gene transfer into germ lines (Van der Putten, et al., *Proc. Natl. Acad. Sci., USA*, 82:6148–6152 (1985)); gene targeting in embryonic stem cells (Thompson, et al., *Cell*, 56:313–321 (1989)); electroporation of embryos (Lo, *Mol Cell. Biol.*, 3:1803–1814 (1983)); and sperm-mediated gene transfer (Lavitrano, et al., *Cell*, 57:717–723 (1989)); etc. For a review of such techniques, see Gordon, Transgenic Animals, *Intl. Rev. Cytol.*, 115:171–229 (1989), which is incorporated by reference herein in its entirety.

Figure 1:
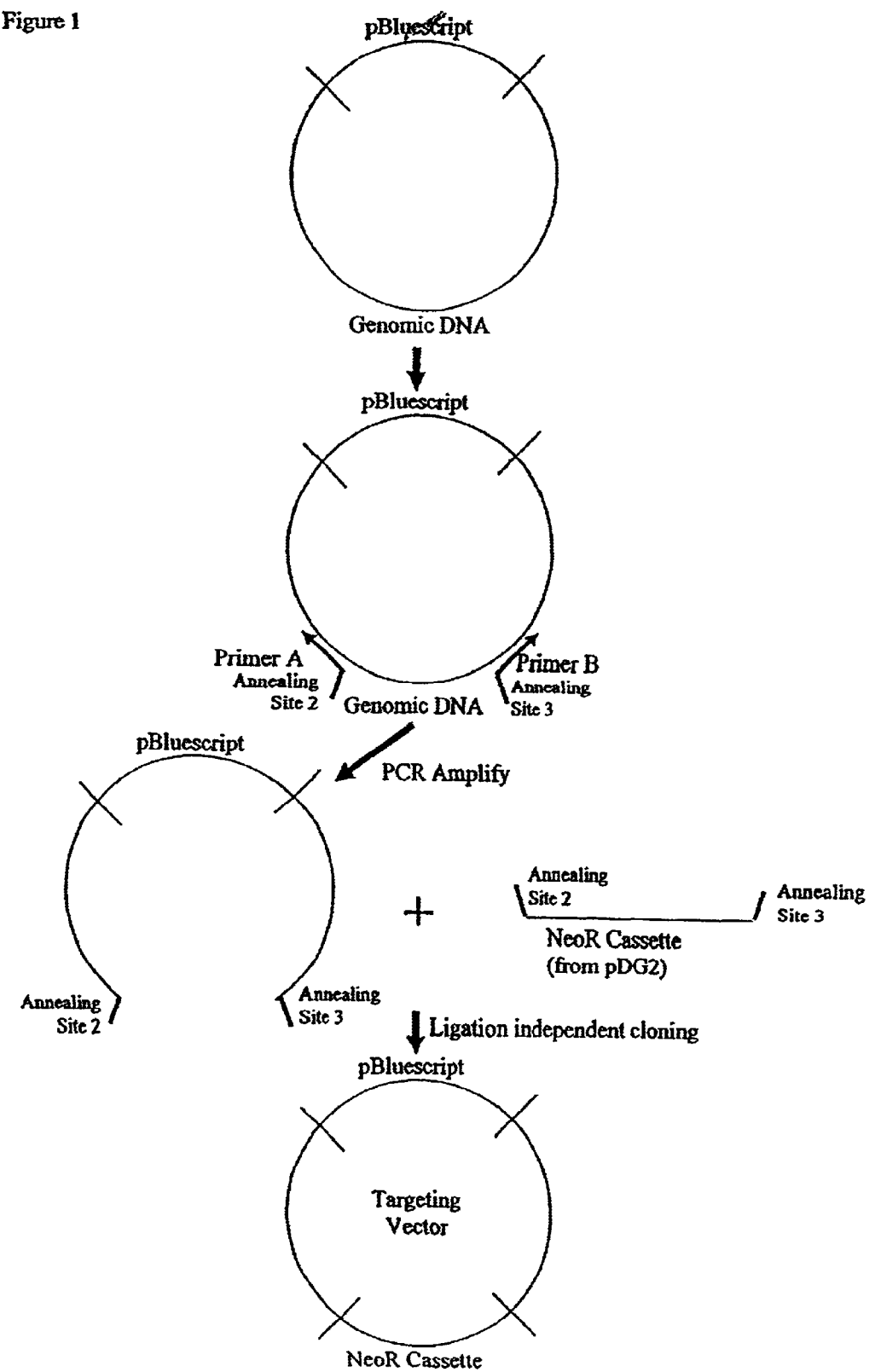
FIG. 1 is a schematic depicting one method of constructing a targeting vector of the present invention. The plasmid PCR method is described in Examples 9 and 10.

In a preferred embodiment, homologous recombination is used to generate the knockout mice of the present invention. Preferably, the construct is generated in two steps by (1) amplifying (for example, using long-range PCR) sequences homologous to the target sequence, and (2) inserting another polynucleotide (for example a selectable marker) into the PCR product so that it is flanked by the homologous sequences. Typically, the vector is a plasmid from a plasmid genomic library. The completed construct is also typically a circular plasmid. Thus, as shown in FIG. 1, using long-range PCR with "outwardly pointing" oligonucleotides results in a vector into which a selectable marker can easily be inserted, preferably by ligation-independent cloning. The construct can then be introduced into ES cells, where it can disrupt the function of the homologous target sequence.

Homologous recombination may also be used to knockout genes in stem cells, and other cell types, which are not totipotent embryonic stem cells. By way of example, stem cells may be myeloid, lymphoid, or neural progenitor and precursor cells. Such transgenic cells may be particularly useful in the study of target gene function in individual developmental pathways. Stem cells may be derived from any vertebrate species, such as mouse, rat, dog, cat, pig, rabbit, human, non-human primates and the like.

In cells which are not totipotent it may be desirable to knock out both copies of the target using methods which are known in the art. For example, cells comprising homologous recombination at a target locus which have been selected for expression of a positive selection marker (e.g., Neor) and screened for non-random integration, can be further selected for multiple copies of the selectable marker gene by exposure to elevated levels of the selective agent (e.g., G418). The cells are then analyzed for homozygosity at the target locus. Alternatively, a second construct can be generated with a different positive selection marker inserted between the two homologous sequences. The two constructs can be introduced into the cell either sequentially or simultaneously, followed by appropriate selection for each of the positive marker genes. The final cell is screened for homologous recombination of both alleles of the target.

In another aspect, two separate fragments of a clone of interest are amplified and inserted into a vector containing a positive selection marker using ligation-independent cloning techniques. In this embodiment, the clone of interest is generally from a phage library and is identified and isolated using PCR techniques. The ligation-independent cloning can be performed in two steps or in a single step.

According to a preferred method, constructs are used having multiple sites where 5'-3' single-stranded regions can be created. These constructs, preferably plasmids, include a vector capable of directional, four-way ligation-independent cloning.

The constructs typically include a sequence encoding a positive selection marker such as a gene encoding neomycin resistance; a restriction enzyme site on either side of the positive selection marker and a sequence flanking the restriction enzyme sites which does not contain one of the four base pairs. This configuration allows single-stranded ends to be created in the sequence by digesting the construct with the appropriate restriction enzyme and treating the fragments with a compound having exonuclease activity, for example T4 DNA polymerase.

In one preferred embodiment, a construct suitable for introducing targeted mutations into ES cells is prepared directly from a plasmid genomic library. Using long-range PCR with specific primers, a sequence of interest is identified and isolated from the plasmid library in a single step. Following isolation of this sequence, a second polynucleotide that will disrupt the target sequence can be readily inserted between two regions encoding the sequence of interest. Using this direct method a targeted construct can be created in as little as 72 hours. In another embodiment, a targeted construct is prepared after identification of a clone of interest in a phage genomic library as described in detail below.

The methods described herein obviate the need for hybridization isolation, restriction mapping and multiple cloning steps. Moreover, the function of any gene can be determined using these methods. For example, a short sequence (e.g., EST) can be used to design oligonucleotide probes. These probes can be used in the direct amplification procedure to create constructs or can be used to screen genomic or cDNA libraries for longer full-length genes. Thus, it is contemplated that any gene can be quickly and efficiently prepared for use in ES cells.

In a preferred embodiment, constructs are prepared directly from a plasmid genomic library. The library can be produced by any method known in the art. Preferably, DNA from mouse ES cells is isolated and treated with a restriction endonuclease which cleaves the DNA into fragments. The DNA fragments are then inserted into a vector, for example a bacteriophage or phagemid (e.g., Lamda ZAP™, Stratagene, La Jolla, Calif.) systems. When the library is created in the ZAP™ system, the DNA fragments are preferably between about 5 and about 20 kilobases.

Preferably, the organism(s) from which the libraries are made will have no discernible disease or phenotypic effects. Preferably, the library is a mouse library. This DNA may be obtained from any cell source or body fluid. Non-limiting examples of cell sources available in clinical practice include ES cells, liver, kidney, blood cells, buccal cells, cerviovaginal cells, epithelial cells from urine, fetal cells, or any cells present in tissue obtained by biopsy. Body fluids include urine, blood cerebrospinal fluid (CSF), and tissue exudates at the site of infection or inflammation. DNA extracted from the cells or body fluid using any method known in the art. Preferably, the DNA is extracted by adding 5 ml of lysis buffer (10 mM Tris-HCl pH 7.5), 10 mM EDTA (pH 8.0), 10 mM NaCl, 0.5% SDS and 1 mg/ml Proteinase K) to a confluent 100 mm plate of embryonic stem cells. The cells are then incubated at about 60° C. for several hours or until fully lysed. Genomic DNA is purified from the lysed cells by several rounds of gentle phenol:chloroform extraction followed by an ethanol precipitation. For convenience, the genomic library can be arrayed into pools.

In a preferred embodiment, a sequence of interest is identified from the plasmid library using oligonucleotide primers and long-range PCR. Typically, the primers are outwardly-pointing primers which are designed based on sequence information obtained from a partial gene sequence, e.g., a cDNA or an EST sequence. As depicted for example in FIG. 1, the product will be a linear fragment that excludes the region which is located between each primer.

PCR conditions found to be suitable are described below in the Examples. It will be understood that optimal PCR conditions can be readily determined by those skilled in the art. (See, e.g., *PCR 2: A Practical Approach* (1995) eds. M. J. McPherson, B. D. Hames and G. R. Taylor, IRL Press, Oxford; Yu, et al., *Methods Mol. Bio.*, 58:335–9 (1996); Munroe, et al., *Proc. Nat'l Acad. Sci., USA*, 92:2209–13 (1995)). PCR screening of libraries eliminates many of the problems and time-delay associated with conventional hybridization screening in which the library must be plated, filters made, radioactive probes prepared and hybridization conditions established. PCR screening requires only oligonucleotide primers to sequences (genes) of interest. PCR products can be purified by a variety of methods, including but not limited to, microfiltration, dialysis, gel electrophoresis and the like. It may be desirable to remove the polymerase used in PCR so that no new DNA synthesis can occur. Suitable thermostable DNA polymerases are commercially available, for example, Vent™ DNA Polymerase (New England Biolabs), Deep Vent™ DNA Polymerase (new England Biolabs), HotTub™ DNA Polymerase (Amersham), Thermo Sequenase™ (Amersham), rBst™ DNA Polymerase (Epicenter), Pfu™ DNA Polymerase (Stratagene), Amplitaq Gold™ (Perkin Elmer), and Expand™ (Boehringer-Mannheim).

To form the completed construct, a sequence which will disrupt the target sequence is inserted into the PCR-amplified product. For example, as described herein, the direct method involves joining the long-range PCR product (ie., the vector) and one fragment (i.e., a gene encoding a selectable marker). As discussed above, the vector contains two different sequence regions homologous to the target DNA sequence. Preferably, the vector also contains a sequence encoding a selectable marker, such as ampicillin. The vector and fragment are designed so that, when treated to form single stranded ends, they will anneal such that the fragment is positioned between the two different regions of substantial homology to the target gene.

Although any method of cloning is suitable, it is preferred that ligation-independent cloning strategies be used to assemble the construct comprising two different homologous regions flanking a selectable marker. Ligation-independent cloning (LIC) is a strategy for the directional cloning of polynucleotides without the use of kinases or ligases. (See, e.g., Aslanidis et al., *Nucleic Acids Res.*, 18:6069–74 (1990); Rashtchian, *Current Opin. Biotech.*, 6:30–36 (1995)). Single-stranded tails (also referred to as cloning sites or annealing sequences) are created in LIC vectors, usually by treating the vector (at a digested restriction enzyme site) with T4 DNA polymerase in the presence of only one dNTP. The 3' to 5' exonuclease activity of T4 DNA polymerase removes nucleotides until it encounters a residue corresponding to the single dNTP present in the reaction mix. At this point, the 5' to 3' polymerase activity of the enzyme counteracts the exonuclease activity to prevent further excision. The vector is designed such that the single-stranded tails created are non-complementary. For example, in the pDG2 vector, none of the single-stranded tails of the four annealing sites are complementary to each other. PCR products are created by building appropriate 5' extensions into oligonucleotide primers. The PCR product is purified to remove dNTPs (and original plasmid if it was used as template) and then treated with T4 DNA polymerase in the presence of the appropriate dNTP to generate the specific vector-compatible overhangs. Cloning occurs by annealing of the compatible tails. Single-stranded tails are created at the ends of the clone fragments, for example using chemical or enzymatic means. Complementary tails are created on the vector; however, to prevent annealing of the vector without insert, the vector tails are not complementary to each other. The length of the tails is at least about 5 nucleotides, preferably at least about 12 nucleotides, even more preferably at least about 20 nucleotides.

In one embodiment, placing the overlapping vector and fragment(s) in the same reaction is sufficient to anneal them. Alternatively, the complementary sequences are combined, heated and allowed to slowly cool. Preferably the heating step is between about 60° C. and about 100° C., more preferably between about 60° C. and 80° C., and even more preferably between 60° C. and 70° C. The heated reactions are then allowed to cool. Generally, cooling occurs rather slowly, for instance the reactions are generally at about room temperature after about an hour. The cooling must be sufficiently slow as to allow annealing. The annealed fragment/vector can be used immediately, or stored frozen at −20° C. until use.

Further, annealing can be performed by adjusting the salt and temperature to achieve suitable conditions. Hybridization reactions can be performed in solutions ranging from about 10 mM NaCl to about 600 mM NaCl, at temperatures ranging from about 37° C. to about 65° C. It will be understood that the stringency of the hybridization reaction is determined by both the salt concentration and the temperature. For instance, a hybridization performed in 10 mM salt at 37° C. may be of similar stringency to one performed in 500 mM salt at 65° C. For the present invention, any hybridization conditions may be used that form hybrids between homologous complementary sequences.

As shown in FIG. 1, in one embodiment, a construct is made after using any of these annealing procedure where the vector portion contains the two different regions of substantial homology to the target gene (amplified from the plasmid library using long-range PCR) and the fragment is a gene encoding a selectable marker.

After annealing, the construct is transformed into competent *E. coli* cells by methods known in the art, to amplify the construct. The isolated construct is then ready for introduction into ES cells.

In another embodiment, a clone of interest is identified in a pooled genomic library using PCR. In one embodiment, the PCR conditions are such that a gene encoding a selectable marker can be inserted directly into the positively identified clone. The marker is positioned between two different sequences having substantial homology to the target DNA.

Genomic phage libraries can be prepared by any method known in the art. Preferably, a mouse embryonic stem cell library is prepared in lambda phage by cleaving genomic DNA into fragments of approximately 20 kilobases in length. The fragments are then inserted into any suitable lambda cloning vector, for example lambda Fix E or lambda Dash II (Stratagene, La Jolla, Calif.)

In order to quickly and efficiently screen a large number of clones from a library, pools may be created of plated libraries. In a preferred embodiment, a genomic lambda phage library is plated at a density of approximately 1,000 clones (plaques) per plate. Sufficient plates are created to represent the entire genome of the organism several times over. For example, approximately 1 million clones (1000 plates) will yield approximately 8 genome equivalents. The plaques are then collected, for example by overlaying the plate with a buffer solution, incubating the plates and recollecting the buffer. The amount of buffer used will vary according to the plate size, generally one 100 mm diameter plate will be overlayed with approximately 4 ml of buffer and approximately 2 ml will be collected.

It will be understood that the individual plate lysates can be pooled at any time during this procedure and that they can be pooled in any combinations. For ease in later identification of single clones, however, it is preferable to keep each plate lysate separately and then make a pool. For example, each 2 ml lysate can be placed in a 96 well deep well plate. Pools can then be formed by taking an amount, preferably about 100 □l, from each well and combining them in the well of a new plate. Preferably, 100 □l of 12 individual plate lysates are combined in one well, forming a 1.2 ml pool representative of 12,000 clones of the library.

Each pool is then PCR-amplified using a set of PCR primers known to amplify the target gene. The target gene can be a known full-length gene or, more preferably, a partial cDNA sequence obtained from publicly available nucleic acid sequence databases such as GenBank or EMBL. These databases include partial cDNA sequences known as expressed sequence tags (ESTs). The oligonucleotide PCR primers can be isolated from any organism by any method known in the art or, preferably, synthesized by chemical means.

Once a positive clone of the target gene has been identified in a genomic library, two fragments encoding separate portions of the target gene must be generated. In other words, the flanking regions of the small known region of the target (e.g., EST) are generated. Although the size of each flanking region is not critical and can range from as few as 100 base pairs to as many as 100 kb, preferably each flanking fragment is greater than about 1 kb in length, more preferably between about 1 and about 10 kb, and even more preferably between about 1 and about 5 kb. One of skill in the art will recognize that although larger fragments may increase the number of homologous recombination events in ES cells, larger fragments will also be more difficult to clone.

In one embodiment, one of the oligonucleotide PCR primers used to amplify a flanking fragment is specific for the library cloning vector, for example lambda phage. Therefore, if the library is a lambda phage library, primers specific for the lambda phage arms can be used in conjunction with primers specific for the positive clone to generate long flanking fragments. Multiple PCR reactions can be set up to test different combinations of primers. Preferably, the primers used will generate flanking sequences between about 2 and about 6 kb in length.

Preferably, the oligonucleotide primers are designed with 5' sequences complementary to the vector into which the fragments will be cloned. In addition, the primers are also designed so that the flanking fragments will be in the proper 3'-5' orientation with respect to the vector and each other when the construct is assembled.

Thus, using PCR-based methods, for example, positive clones can be identified by visualization of a band on an electrophoretic gel.

Figure 3A:
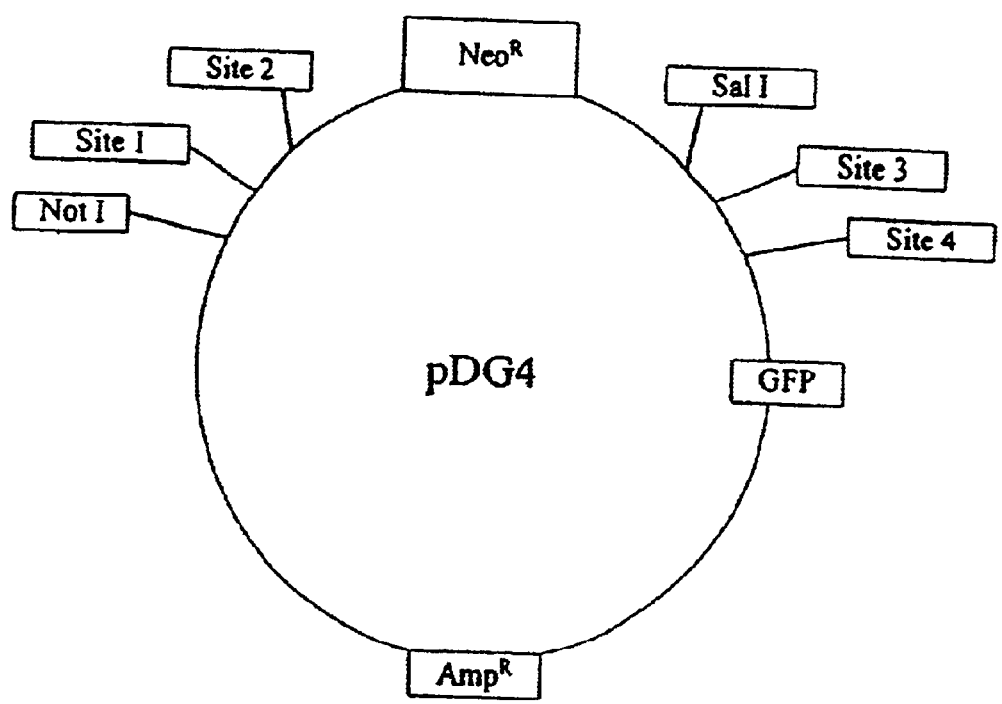
FIG. 3A is schematic depicting the pDG4 vector. The vector contains an ampicillin resistance gene, a neomycin (Neo$^r$) gene and a green fluorescent protein (GFP) gene. On each side of the Neo$^r$ gene are two sites for ligation-independent cloning along with restriction enzyme recognition sites. The sequence of pDG4 is shown in FIG. 3B and SEQ ID NO:2.
Figure 6:
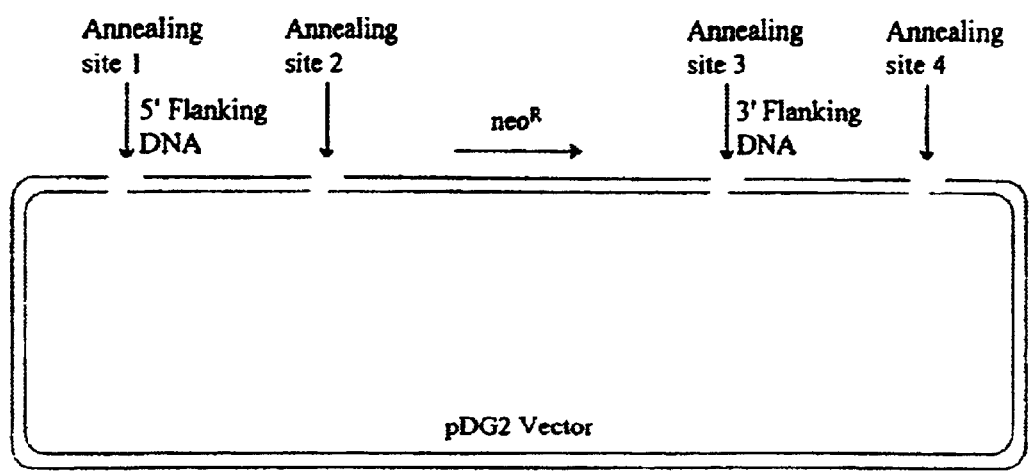
FIG. 6 shows the arrangement of 5' and 3' flanking DNA relative to annealing sites 1, 2, 3 and 4 within the pDG2 vector during an annealing reaction.
Figure 7:
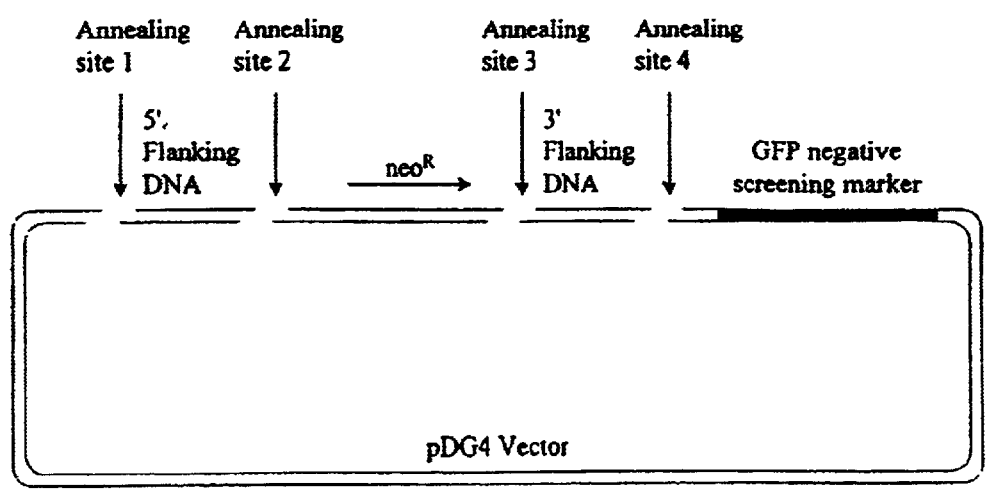
FIG. 7 shows the arrangement of 5' and 3' flanking DNA relative to annealing sites 1, 2, 3 and 4 and the GFP screening marker within the pDG4 vector during an annealing reaction.

In one aspect, the cloning involves a vector and two fragments. The vector contains a positive selection marker, preferably Neor, and cloning sites on each side of the positive selection marker for two different regions of the target gene. Optionally, the vector also contains a sequence coding for a screening marker (reporter gene), preferably, positioned opposite the positive selection marker. The screening marker will be positioned outside the flanking regions of homologous sequences. FIG. 3A shows one embodiment of the vector with the screening marker, GFP, positioned on one side of the vector. However, the screening marker can be positioned anywhere between Not I and Site 4 on the side opposite the positive selection marker, Neo$^r$.

One example of a suitable vector is the plasmid vector shown in FIG. 2 having the sequence of SEQ ID NO: 1. The specific nucleic acid ligation-independent cloning sites (also referred to herein as annealing sites) labeled "sites 1, 2, 3 or 4" in FIG. 1 are also shown herein. Generally, the cloning sites are lacking at least one type of base, i.e., thymine (T), guanine (G), cytosine (C) or adenine (A). Accordingly, reacting the vector with an enzyme that acts as both a polymerase and exonuclease in presence of only the one missing nucleotide will create an overhang. For example, T4 DNA polymerase acts as both a 3'-5' exonuclease and a polymerase. Thus, when there are insufficient nucleotides available for the polymerase activity, T4 will act as an exonuclease. Specific overhangs can therefore be created by reacting the pDG2 vector with T4 DNA polymerase in the presence of dTTP only. Other enzymes useful in the practice of this invention will be known to those in the art, for instance uracil DNA glycosylase (UDG) (See, e.g., WO 93/18175). The vector exemplified herein has an overhand of 24 nucleotides. It will be known by those skilled in the art that as few as 5 nucleotides are required for successful ligation independent cloning.

In another embodiment, a construct is assembled in a two-step cloning protocol. In the first step, each cloning region of homology is separately cloned into two of the annealing sites of the vector. For example, an "upstream" region of homology is cloned into annealing sites 1 and 2 while a separate cloning, a "downstream" region of homology is cloned into annealing sites 3 and 4. Once clones containing each single region of homology are identified, a targeting construct containing both regions of homology can be created by digesting each clone with restriction enzymes where one enzyme digests outside of annealing site 1 (e.g., Not I in FIG. 2A) and another enzyme digests between the positive selection marker and annealing site 3 (e.g., Sal I in FIG. 2A). The fragments containing the flanking homology regions from each construct will be purified (e.g., by gel electrophoresis) and combined using standard ligation techniques known in the art, to produce the resulting targeting construct.

In yet another embodiment, a construct according to one aspect of the present invention can be formed in a single-step, four-way ligation procedure. The vector and fragments are treated as described above. Briefly, the vector is treated to form two pieces, each piece having a single-stranded tail of specific sequence on each end. Likewise, the PCR-amplified flanking fragments are also treated to form single-stranded tails complementary to those of the vector pieces. The treated vector pieces and fragments are combined and allowed to anneal as described above. Because of the specificity of the single-stranded tails, the final construct will contain the fragments separated by the positive selection marker in the proper orientation.

The final plasmid constructs are amplified in bacteria, purified and can then be introduced into ES cells, or stored frozen at −20° C. until use. Where so desired, the vector is introduced into an embryonic stem cell line (e.g., by electroporation) and cells in which the introduced DNA has homologously recombined with the endogenous DNA are selected (see e.g., Li, et al., *Cell,* 69:91526 (1992)). Successful recombination may be verified using various techniques known in the art, such as PCR and/or Southern analysis. Typically, several hundred individual colonies are selected following drug selection in G418 (for Neo cassettes), expanded for DNA preparation and screened for homologous recombination by PCR analysis. The PCR screening procedure uses a target gene specific oligonucleotide that is not present on the targeting vector and an oligonucleotide corresponding to the Neo (or other selectable marker) cassette. The selection of oligonucleotides outside the targeting vector is used to differentiate homologous recombinants from random integrations of the targeting vector. In general, four independent target gene specific oligonucleotides not present on the targeting vector are tested on wild type ES cell DNA in combination with target gene specific oligonucleotides that are adjacent to the insertion site of the Neo (FIG. 9). Oligonucleotides producing background bands or failing to give the predicted size product are eliminated. A single target gene specific oligonucleotide is selected and paired with an oligonucleotide corresponding to the Neo cassette. ES cells that are PCR positive in this screen are confirmed by a second PCR experiment that utilizes a different pair of target gene specific and Neo gene (or other selectable marker) specific oligonucleotides that are adjacent to, but distinct from, the original oligonucleotide pair. In addition, this protocol may be repeated using oligonucleotides specific for target gene sequences located on the opposite side of the selectable marker in conjunction with a marker specific oligonucleotide. In this way proper integration of both homologous sequences of the targeting vector is verified.

Southern blot hybridization may also be used to confirm the ES cell targeting event using a probe that is not contained on the targeting vector but is adjacent to the predicted crossover site of homologous recombination. Southern blot experiments testing for homologous recombination should detect two distinct bands representing the wild type chromosome and mutant gene targeted allele. High molecular weight genomic DNA is prepared from control ES cell parental lines and ES cell lines that are PCR positive for homologous recombination. The DNA is digested with a restriction enzyme (EcoRi) that has been demonstrated by restriction mapping to not cut the targeting vector within the arm of the target gene DNA homology and to be diagnostic of homologous recombination. As an EcoRl site is present in the Neo gene, a homologous recombination event should result in the insertion of the Neo cassette and the addition of the EcoRl site. The addition of this site is predicted to result in an overall reduction in size of the band hybridizing to the probe. The digested DNA is separated on a 1% TAE Agarose gel, transferred to a nylon membrane, crosslinked with a UV light (StrataLinker) and hybridized with a 32-P labeled DNA probe. This probe does not hybridize to DNA sequences that are on the targeting vector but to a position that is adjacent to the site of homologous integration.

Selected cells are then injected into a blastocyst (or other stage of development suitable for the purposes of creating a viable animal, such as, for example, a morula) of an animal (e.g., a mouse) to form chimeras (see e.g., Bradley, A. in *Teratocarcinomas and Embryonic Stem Cells: A Practical Approach*, E. J. Robertson, ed., IRL, Oxford, pp. 113–152 (1987)). Alternatively, selected ES cells can be allowed to aggregate with dissociated mouse embryo cells to form the aggregation chimera. A chimeric embryo can then be implanted into a suitable pseudopregnant female foster animal and the embryo brought to term. Chimeric progeny harbouring the homologously recombined DNA in their germ cells can be used to breed animals in which all cells of the animal contain the homologously recombined DNA. In one embodiment, chimeric progeny mice are used to generate a mouse with a heterozygous disruption in the target gene. Heterozygous knockout mice can then be mated. It is well know in the art that typically ¼ of the offspring of such matings will have a homozygous disruption in the target gene.

The heterozygous and homozygous knockout mice can then be compared to normal, wild type mice to determine whether disruption of the target gene causes phenotypic changes, especially pathological changes. For example, heterozygous and homozygous mice may be evaluated for phenotypic changes by physical examination, necropsy, histology, clinical chemistry, complete blood count, body weight, organ weights, and cytological evaluation of bone marrow.

In one embodiment, the phenotype (or phenotypic change) associated with a disruption in the target gene is placed into or stored in a database. Preferably, the database includes: (i) genotypic data (e.g., identification of the disrupted gene) and (ii) phenotypic data (e.g., phenotype(s) resulting from the gene disruption) associated with the genotypic data. The database is preferably electronic. In addition, the database is preferably combined with a search tool so that the database is searchable.

The present invention further contemplates conditional knockout animals, such as those produced using recombination methods. Bacteriophage P1 Cre recombinase and flp recombinase from yeast plasmids are two non-limiting examples of site-specific DNA recombinase enzymes which cleave DNA at specific target sites (lox P sites for cre recombinase and frt sites for flp recombinase) and catalyze a ligation of this DNA to a second cleaved site. A large number of suitable alternative site-specific recombinases have been described, and their genes can be used in accordance with the method of the present invention. Such recombinases include the Int recombinase of bacteriophage λ (with or without Xis) (Weisberg, R. et. al., in *Lambda II*, (Hendrix, R., et al., Eds.), Cold Spring Harbor Press, Cold Spring Harbor, N.Y., pp. 211–50 (1983), herein incorporated by reference); TpnI and the β-lactamase transposons (Mercier, et al., *J. Bacteriol.*, 172:3745–57 (1990)); the Tn3 resolvase (Flanagan & Fennewald *J. Molec. Biol.*, 206:295–304 (1989); Stark, et al., *Cell*, 58:779–90 (1989)); the yeast recombinases (Matsuzaki, et al., *J. Bacteriol.*, 172:610–18 (1990)); the *B. subtilis* SpoIVC recombinase (Sato, et al., *J. Bacteriol.* 172:1092–98 (1990)); the Flp recombinase (Schwartz & Sadowski, *J. Molec.Biol.*, 205:647–658 (1989); Parsons, et al., *J. Biol. Chem.*, 265:4527–33 (1990); Golic & Lindquist, *Cell*, 59:499–509 (1989); Amin, et al., *J. Molec. Biol.*, 214:55–72 (1990)); the Hin recombinase (Glasgow, et al., *J. Biol. Chem.*, 264:10072–82 (1989)); immunoglobulin recombinases (Malynn, et al., *Cell*, 54:453–460 (1988)); and the Cin recombinase (Haffter & Bickle, *EMBO J.*, 7:3991–3996 (1988); Hubner, et al., *J. Molec. Biol.*, 205:493–500 (1989)), all herein incorporated by reference. Such systems are discussed by Echols (*J. Biol. Chem.* 265:14697–14700 (1990)); de Villartay (*Nature*, 335:170–74 (1988)); Craig, (*Ann. Rev. Genet.*, 22:77–105 (1988)); Poyart-Salmeron, et al., (*EMBO J.* 8:2425–33 (1989)); Hunger-Bertling, et al. (*Mol Cell. Biochem.*, 92:107–16 (1990)); and Cregg & Madden (*Mol. Gen. Genet.*, 219:320–23 (1989)), all herein incorporated by reference.

Cre has been purified to homogeneity, and its reaction with the loxP site has been extensively characterized (Abremski & Hess *J. Mol. Biol.* 259:1509–14 (1984), herein incorporated by reference). Cre protein has a molecular weight of 35, 000 and can be obtained commercially from New England Nuclear/Du Pont. The cre gene (which encodes the Cre protein) has been cloned and expressed (Abremski, et al. *Cell* 32:1301–11 (1983), herein incorporated by reference). The Cre protein mediates recombination between two loxP sequences (Sternberg, et al. *Cold Spring Harbor Symp. Quant. Biol.* 45:297–309 (1981)), which may be present on the same or different DNA molecule. Because the internal spacer sequence of the loxP site is asymmetrical, two loxP sites can exhibit directionality relative to one another (Hoess & Abremski *Proc. Natl. Acad Sci. U.S.A.* 81:1026–29 (1984)). Thus, when two sites on the same DNA molecule are in a directly repeated orientation, Cre will excise the DNA between the sites (Abremski, et al. *Cell* 32:1301–11 (1983)). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites. In addition, recombinase action can result in reciprocal exchange of regions distal to the target site when targets are present on separate DNA molecules.

Recombinases have important application for characterizing gene function in knockout models. When the constructs described herein are used to disrupt target genes, a fusion transcript can be produced when insertion of the positive selection marker occurs downstream (3') of the translation initiation site of the target gene. The fusion transcript could result in some level of protein expression with unknown consequence. It has been suggested that insertion of a positive selection marker gene can affect the expression of nearby genes. These effects may in make it difficult to determine gene function after a knockout event since one could not discern whether a given phenotype is associated with the inactivation of a gene, or the transcription of nearby genes. Both potential problems are solved by exploiting recombinase activity. When the positive selection marker is flanked by recombinase sites in the same orientation, the addition of the corresponding recombinase will result in the removal of the positive selection marker. In this way, effects caused by the positive selection marker or expression of fusion transcripts are avoided.

In one embodiment, purified recombinase enzyme is provided to the cell by direct microinjection. In another embodiment, recombinase is expressed from a co-transfected construct or vector in which the recombinase gene is operably linked to a functional promoter. An additional aspect of this embodiment is the use of tissue-specific or inducible recombinase constructs which allow the choice of when and where recombination occurs. One method for practicing the inducible forms of recombinase-mediated recombination involves the use of vectors that use inducible or tissue-specific promoters or other gene regulatory elements to express the desired recombinase activity. The inducible expression elements are preferably operatively positioned to allow the inducible control or activation of expression of the desired recombinase activity. Examples of such inducible promoters or other gene regulatory elements include, but are not limited to, tetracycline, metallothionine, ecdysone, and other steroid-responsive promoters, rapamycin responsive promoters, and the like (No, et al. *Proc. Natl. Acad. Sci. USA,* 93:3346–51 (1996); Furth, et al. *Proc. Natl. Acad. Sci. USA,* 91:9302–6 (1994)). Additional control elements that can be used include promoters requiring specific transcription factors such as viral, promoters. Vectors incorporating such promoters would only express recombinase activity in cells that express the necessary transcription factors.

Other methods known in the art may be used to produce the transgenic cells and knockout mice of the present invention. For example, the methods described in U.S. Pat. Nos. 5,464,764; 5,487,992; 5,627,059; and 5,631,153 may be used to produce a transgenic cell or knockout mice comprising a disruption in a gene encoding a retina-specific nuclear receptor as provided by the present invention.

Models for Disease

The cell- and animal-based systems described herein can be utilized as models for diseases. Animals of any species, including, but not limited to, mice, rats, rabbits, guinea pigs, pigs, micro-pigs, goats, and non-human primates, e.g., baboons, monkeys, and chimpanzees may be used to generate disease animal models. In addition, cells from humans may be used. These systems may be used in a variety of applications. For example, the cell- and animal-based model systems may be used to further characterize retina-specific nuclear receptor genes. Such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

Cell-based systems may be used to identify compounds which may act to ameliorate disease symptoms. For example, such cell systems may be exposed to a compound suspected of exhibiting an ability to ameliorate disease symptoms, at a sufficient concentration and for a time sufficient to elicit such an amelioration of disease symptoms in the exposed cells. After exposure, the cells are examined to determine whether one or more of the disease cellular phenotypes has been altered to resemble a more normal or more wild type, non-disease phenotype.

In addition, animal-based disease systems, such as those described herein, may be used to identify compounds capable of ameliorating disease symptoms. Such animal models may be used as test substrates for the identification of drugs, pharmaceuticals, therapies, and interventions which may be effective in treating a disease or other phenotypic characteristic of the animal. For example, animal models may be exposed to a compound or agent suspected of exhibiting an ability to ameliorate disease symptoms, at a sufficient concentration and for a time sufficient to elicit such an amelioration of disease symptoms in the exposed animals. The response of the animals to the exposure may be monitored by assessing the reversal of disorders associated with the disease. Exposure may involve treating mother animals during gestation of the model animals described herein, thereby exposing embryos or fetuses to the compound or agent which may prevent or ameliorate the disease or phenotype. Neonatal, juvenile, and adult animals can also be exposed.

More particularly, using the animal models of the invention, specifically, knockout mice, methods of identifying compounds are provided, preferably, on the basis of the ability of the compounds to affect physiological, histological or behavioral phenotypes associated with a disruption in a gene that encodes a retina-specific nuclear receptor.

In one embodiment, the present invention provides a method of identifying agents having an effect on retina-specific nuclear receptor expression or function. The method includes administering an effective amount of the agent to a vertebrate animal, preferably a mouse, having a disruption in a gene encoding a retina-specific nuclear receptor. The method includes measuring a physiological response of the animal, for example, to the agent, and comparing the physiological response of such animal to a control animal, wherein the physiological response of the animal comprising a gene encoding a retina-specific nuclear receptor as compared to the control animal indicates the specificity of the agent. A "physiological response" is any biological or physical parameter of an animal which can be measured. Molecular assays (e.g., gene transcription, protein production and degradation rates), physical parameters (e.g., exercise physiology tests, measurement of various parameters of respiration, measurement of heart rate or blood pressure, measurement of bleeding time, aPTT.T, or TT), and cellular assays (e.g, . immunohistochemical assays of cell surface markers, or the ability of cells to aggregate or proliferate) can be used to assess a physiological response.

The animals and cells of the present invention may by utilized as models for diseases, disorders, or conditions associated with phenotypes relating to a disruption in a gene encoding a retina-specific nuclear receptor.

The present invention also provides a unique animal model for testing and developing new treatments relating to the behavioral phenotypes. Analysis of the behavioral phenotype allows for the development of an animal model useful for testing, for instance, the efficacy of proposed genetic and pharmacological therapies for human genetic diseases, such as neurological, neuropsychological, or psychotic illnesses.

A statistical analysis of the various behaviors measured can be carried out using any conventional statistical program routinely used by those skilled in the art (such as, for example, "Analysis of Variance" or ANOVA). A "p" value of about 0.05 or less is generally considered to be statistically significant, although slightly higher p values may still be indicative of statistically significant differences. To statistically analyze abnormal behavior, a comparison is made between the behavior of a transgenic animal (or a group thereof) to the behavior of a wild-type mouse (or a group thereof), typically under certain prescribed conditions. "Abnormal behavior" as used herein refers to behavior exhibited by an animal having a disruption in the target gene, e.g. transgenic animal, which differs from an animal without a disruption in the target gene, e.g. wild-type mouse. Abnormal behavior consists of any number of standard behaviors that can be objectively measured (or observed) and compared. In the case of comparison, it is preferred that the change be statistically significant to confirm that there is indeed a meaningful behavioral difference between the knockout animal and the wild-type control animal. Examples of behaviors which may be measured or observed include, but are not limited to, ataxia, rapid limb movement, eye movement, breathing, motor activity, cognition, emotional behaviors, social behaviors, hyperactivity, hypersensitivity, anxiety, impaired learning, abnormal reward behavior, and abnormal social interaction, such as aggression A series of tests may be used to measure the behavioral phenotype of the animal models of the present invention, including neurological and neuropsychological tests to identify abnormal behavior. These tests may be used to measure abnormal behavior relating to, for example, learning and memory, eating, pain, aggression, sexual reproduction, anxiety, depression, schizophrenia, and drug abuse. (See, e.g., Crawley and Paylor, *Hormones and Behavior* 31:197–211 (1997)).

The social interaction test involves exposing a mouse to other animals in a variety of settings. The social behaviors of the animals (e.g., touching, climbing, sniffing, and mating) are subsequently evaluated. Differences in behaviors can then be statistically analyzed and compared (See, e.g., S. E. File, et al., *Pharmacol. Bioch. Behav.* 22:941–944 (1985); R. R. Holson, *Phys. Behav.* 37:239–247 (1986)). Examplary behavioral tests include the following.

The mouse startle response test typically involves exposing the animal to a sensory (typically auditory) stimulus and measuring the startle response of the animal (see, e.g., M. A. Geyer, et al., *Brain Res. Bull.* 25:485498 (1990); Paylor and Crawley, *Psychopharmacology* 132:169–180 (1997)). A pre-pulse inhibition test can also be used, in which the percent inhibition (from a normal startle response) is measured by "cueing" the animal first with a brief low-intensity pre-pulse prior to the startle pulse.

The electric shock test generally involves exposure to an electrified surface and measurement of subsequent behaviors such as, for example, motor activity, learning, social behaviors. The behaviors are measured and statistically analyzed using standard statistical tests. (See, e.g., G. J. Kant, et al., *Pharm. Bioch. Behav.* 20:793–797 (1984); N. J. Leidenheimer, et al., *Pharmacol. Bioch. Betav.* 30:351–355 (1988)).

The tail-pinch or immobilization test involves applying pressure to the tail of the animal and/or restraining the animal's movements. Motor activity, social behavior, and cognitive behavior are examples of the areas that are measured. (See, e.g., M. Bertolucci D'Angic, et al., *Neurochem.* 55:1208–1214 (1990)).

The novelty test generally comprises exposure to a novel environment and/or novel objects. The animal's motor behavior in the novel environment and/or around the novel object are measured and statistically analyzed. (See, e.g., D. K. Reinstein, et al., *Pharm. Bioch. Behav.* 30 17:193–202 (1982); B. Poucet, *Behav. Neurosci.* 103:1009–10016 (1989); R. R. Holson, et al., *Phys. Behav.* 37:231–238 (1986)). This test may be used to detect visual processing deficiencies or defects.

The learned helplessness test involves exposure to stresses, for example, noxious stimuli, which cannot be affected by the animal's behavior. The animal's behavior can be statistically analyzed using various standard statistical tests. (See, e.g., A. Leshner, et al., *Behav. Neural Biol.* 26:497–501 (1979)).

Alternatively, a tail suspension test may be used, in which the "immobile" time of the mouse is measured when suspended "upside-down" by its tail. This is a measure of whether the animal struggles, an indicator of depression. In humans, depression is believed to result from feelings of a lack of control over one's life or situation. It is believed that a depressive state can be elicited in animals by repeatedly subjecting them to aversive situations over which they have no control. A condition of "learned helplessness" is eventually reached, in which the animal will stop trying to change its circumstances and simply accept its fate. Animals that stop struggling sooner are believed to be more prone to depression. Studies have shown that the administration of certain antidepressant drugs prior to testing increases the amount of time that animals struggle before giving up.

The Morris water-maze test comprises learning spatial orientations in water and subsequently measuring the animal's behaviors, such as, for example, by counting the number of incorrect choices. The behaviors measured are statistically analyzed using standard statistical tests. (See, e.g., E. M. Spruijt, et al., *Brain Res.* 527:192–197 (1990)).

Alternatively, a Y-shaped maze may be used (see, e.g., McFarland, D. J., *Pharmacology, Biochemistry and Behavior* 32:723–726 (1989); Dellu, F., et al., *Neurobiology of Learning and Memory* 73:31–48 (2000)). The Y-maze is generally believed to be a test of cognitive ability. The dimensions of each arm of the Y-maze can be, for example, approximately 40 cm ×8 cm×20 cm, although other dimensions may be used. Each arm can also have, for example, sixteen equally spaced photobeams to automatically detect movement within the arms. At least two different tests can be performed using such a Y-maze. In a continuous Y-maze paradigm, mice are allowed to explore all three arms of a Y-maze for, e.g., approximately 10 minutes. The animals are continuously tracked using photobeam detection grids, and the data can be used to measure spontaneous alteration and positive bias behavior. Spontaneous alteration refers to the natural tendency of a "normal" animal to visit the least familiar arm of a maze. An alternation is scored when the animal makes two consecutive turns in the same direction, thus representing a sequence of visits to the least recently entered arm of the maze. Position bias determines egocentrically defined responses by measuring the animal's tendency to favor turning in one direction over another. Therefore, the test can detect differences in an animal's ability to navigate on the basis of allocentric or egocentric mechanisms. The two-trial Y-maze memory test measures response to novelty and spatial memory based on a free-choice exploration paradigm. During the first trial (acquisition), the animals are allowed to freely visit two arms of the Y-maze for, e.g., approximately 15 minutes. The third arm is blocked off during this trial. The second trial (retrieval) is performed after an intertrial interval of, e.g., approximately 2 hours. During the retrieval trial, the blocked arm is opened and the animal is allowed access to all three arms for, e.g., approximately 5 minutes. Data are collected during the retrieval trial and analyzed for the number and duration of visits to each arm. Because the three arms of the maze are virtually identical, discrimination between novelty and familiarity is dependent on "environmental" spatial cues around the room relative to the position of each arm. Changes in arm entry and duration of time spent in the novel arm in a transgenic animal model may be indicative of a role of that gene in mediating novelty and recognition processes.

The passive avoidance or shuttle box test generally involves exposure to two or more environments, one of which is noxious, providing a choice to be learned by the animal. Behavioral measures include, for example, response latency, number of correct responses, and consistency of response. (See, e.g., R. Ader, et al., *Psychon. Sci.* 26:125–128 (1972); R. R. Holson, *Phys. Behav.* 37:221–230 (1986)). Alternatively, a zero-maze can be used. In a zero-maze, the animals can, for example, be placed in a closed quadrant of an elevated annular platform having, e.g., 2 open and 2 closed quadrants, and are allowed to explore for approximately 5 minutes. This paradigm exploits an approach-avoidance conflict between normal exploratory activity and an aversion to open spaces in rodents. This test measures anxiety levels and can be used to evaluate the effectiveness of anti-anxiolytic drugs. The time spent in open quadrants versus closed quadrants may be recorded automatically, with, for example, the placement of photobeams at each transition site.

The food avoidance test involves exposure to novel food and objectively measuring, for example, food intake and intake latency. The behaviors measured are statistically analyzed using standard statistical tests. (See, e.g., B. A. Campbell, et al., *J. Comp. Physiol. Psychol.* 67:15–22 (1969)).

The elevated plus-maze test comprises exposure to a maze, without sides, on a platform, the animal's behavior is objectively measured by counting the number of maze entries and maze learning. The behavior is statistically analyzed using standard statistical tests. (See, e.g., H. A. Baldwin, et al., *Brain Res. Bull,* 20:603606 (1988)).

The stimulant-induced hyperactivity test involves injection of stimulant drugs (e.g., amphetamines, cocaine, PCP, and the like), and objectively measuring, for example, motor activity, social interactions, cognitive behavior. The animal's behaviors are statistically analyzed using standard statistical tests. (See, e.g., P. B. S. Clarke, et al., *Psychopharmacology* 96:511–520 (1988); P. Kuczenski, et al., *J. Neuroscience* 11:2703–2712 (1991)).

The self-stimulation test generally comprises providing the mouse with the opportunity to regulate electrical and/or chemical stimuli to its own brain. Behavior is measured by frequency and pattern of self-stimulation. Such behaviors are statistically analyzed using standard statistical tests. (See, e.g., S. Nassif, et al., *Brain Res.,* 332:247–257 (1985); W. L. Isaac, et al., *Behav. Neurosci.* 103:345–355 (1989)).

The reward test involves shaping a variety of behaviors, e.g., motor, cognitive, and social, measuring, for example, rapidity and reliability of behavioral change, and statistically analyzing the behaviors measured. (See, e.g., L. E. Jarrard, et al., Exp. Brain Res. 61:519–530 (1986)).

The DRL (differential reinforcement to low rates of responding) performance test involves exposure to intermittent reward paradigms and measuring the number of proper responses, e.g., lever pressing. Such behavior is statistically analyzed using standard statistical tests. (See, e.g., J. D. Sinden, et al., Behav. Neurosci. 100:320–329 (1986); V. Nalwa, et al., Behav Brain Res. 17:73–76 (1985); and A. J. Nonneman, et al., J. Comp. Physiol. Psych. 95:588–602 (1981)).

The spatial learning test involves exposure to a complex novel environment, measuring the rapidity and extent of spatial learning, and statistically analyzing the behaviors measured. (See, e.g., N. Pitsikas, et al., Pharm. Bioch. Behav. 38:931–934 (1991); B. poucet, et al., Brain Res. 37:269–280 (1990); D. Christie, et al., Brain Res. 37:263–268 (1990); and F. Van Haaren, et al., Behav. Neurosci. 102:481–488 (1988)). Alternatively, an open-field (of) test may be used, in which the greater distance traveled for a given amount of time is a measure of the activity level and anxiety of the animal. When the open field is a novel environment, it is believed that an approach-avoidance situation is created, in which the animal is "torn" between the drive to explore and the drive to protect itself. Because the chamber is lighted and has no places to hide other than the corners, it is expected that a "normal" mouse will spend more time in the corners and around the periphery than it will in the center where there is no place to hide. "Normal" mice will, however, venture into the central regions as they explore more and more of the chamber. It can then be extrapolated that especially anxious mice will spend most of their time in the corners, with relatively little or no exploration of the central region, whereas bold (i.e., less anxious) mice will travel a greater distance, showing little preference for the periphery versus the central region.

The visual, somatosensory and auditory neglect tests generally comprise exposure to a sensory stimulus, objectively measuring, for example, orientating responses, and statistically analyzing the behaviors measured. (See, e.g., J. M. Vargo, et al., Exp. Neurol. 102:199–209 (1988)).

The consummatory behavior test generally comprises feeding and drinking, and objectively measuring quantity of consumption. The behavior measured is statistically analyzed using standard statistical tests. (See, e.g., P. J. Fletcher, et al., Psychopharmacol. 102:301–308 (1990); M. G. Corda, et al., , Proc. Nat'l Acad. Sci. USA 80:2072–2076 (1983)).

A visual discrimination test can also be used to evaluate the visual processing of an animal. One or two similar objects are placed in an open field and the animal is allowed to explore for about 5–10 minutes. The time spent exploring each object (proximity to, i.e., movement within, e.g., about 3–5 cm of the object is considered exploration of an object) is recorded. The animal is then removed from the open field, and the objects are replaced by a similar object and a novel object. The animal is returned to the open field and the percent time spent exploring the novel object over the old object is measured (again, over about a 5–10 minute span). "Normal" animals will typically spend a higher percentage of time exploring the novel object rather than the old object. If a delay is imposed between sampling and testing, the memory task becomes more hippocampal-dependent. If no delay is imposed, the task is more based on simple visual discrimination. This test can also be used for olfactory discrimination, in which the objects (preferably, simple blocks) can be sprayed or otherwise treated to hold an odor. This test can also be used to determine if the animal can make gustatory discriminations; animals that return to the previously eaten food instead of novel food exhibit gustatory neophobia.

A hot plate analgesia test can be used to evaluate an animal's sensitivity to heat or painful stimuli. For example, a mouse can be placed on an approximately 55° C. hot plate and the mouse's response latency (e.g., time to pick up and lick a hind paw) can be recorded. These responses are not reflexes, but rather "higher" responses requiring cortical involvement. This test may be used to evaluate a nociceptive disorder.

An accelerating rotarod test may be used to measure coordination and balance in mice. Animals can be, for example, placed on a rod that acts like a rotating treadmill (or rolling log). The rotarod can be made to rotate slowly at first and then progressively faster until it reaches a speed of, e.g., approximately 60 rpm. The mice must continually reposition themselves in order to avoid falling off. The animals are preferably tested in at least three trials, a minimum of 20 minutes apart. Those mice that are able to stay on the rod the longest are believed to have better coordination and balance.

A metrazol administration test can be used to screen animals for varying susceptibilities to seizures or similar events. For example, a 5 mg/ml solution of metrazol can be infused through the tail vein of a mouse at a rate of, e.g., approximately 0.375 ml/min. The infusion will cause all mice to experience seizures, followed by death. Those mice that enter the seizure stage the soonest are believed to be more prone to seizures. Four distinct physiological stages can be recorded: soon after the start of infusion, the mice will exhibit a noticeable "twitch", followed by a series of seizures, ending in a final tensing of the body known as "tonic extension", which is followed by death.

Target Gene Products

The present invention further contemplates use of the target gene sequence to produce target gene products. Target gene products may include proteins that represent functionally equivalent gene products. Such an equivalent gene product may contain deletions, additions or substitutions of amino acid residues within the amino acid sequence encoded by the gene sequences described herein, but which result in a silent change, thus producing a functionally equivalent target gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous gene products encoded by the target gene sequences. Alternatively, when utilized as part of an assay, "functionally equivalent" may refer to peptides capable of interacting with other cellular or to extracellular molecules in a manner substantially similar to the way in which the corresponding portion of the endogenous gene product would.

Other protein products useful according to the methods of the invention are peptides derived from or based on the target gene produced by recombinant or synthetic means (derived peptides).

Target gene products may be produced by recombinant DNA technology using techniques well known in the art. Thus, methods for preparing the gene polypeptides and peptides of the invention by expressing nucleic acid encoding gene sequences are described herein. Methods which are well known to those skilled in the art can be used to construct expression vectors containing gene protein coding sequences and appropriate transcriptional/translational control signals. These methods include, for example, in vitro recombinant DNA techniques, synthetic techniques and in vivo recombination/genetic recombination (see, e.g., Sambrook, et al., 1989, supra, and Ausubel, et al., 1989, supra). Alternatively, RNA capable of encoding gene protein sequences may be chemically synthesized using, for example, automated synthesizers (see, e.g. Oligonucleotide Synthesis: A Practical Approach, Gait, M. J. ed., IRL Press, Oxford (1984)).

A variety of host-expression vector systems may be utilized to express the gene coding sequences of the invention. Such host-expression systems represent vehicles by which the coding sequences of interest may be produced and subsequently purified, but also represent cells which may, when transformed or transfected with the appropriate nucleotide coding sequences, exhibit the gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing gene protein coding sequences; yeast (e.g. Saccharomyces, Pichia) transformed with recombinant yeast expression vectors containing the gene protein coding sequences; insect cell systems infected with recombinant virus expression vectors (e.g., baculovirus) containing the gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. coli* expression vector pUR278 (Ruther et al., *EMBO J.*, 2:1791–94 (1983)), in which the gene protein coding sequence may be ligated individually into the vector in frame with the lac Z coding region so that a fusion protein is produced; pIN vectors (Inouye & Inouye, *Nucleic Acids Res.*, 13:3101–09 (1985); Van Heeke et al., *J. Biol. Chem.*, 264:5503–9 (1989)); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In a preferred embodiment, full length cDNA sequences are appended with in-frame Bam HI sites at the amino terminus and Eco RI sites at the carboxyl terminus using standard PCR methodologies (Innis, et al. (eds) PCR Protocols: A Guide to Methods and Applications, Academic Press, San Diego (1990)) and ligated into the pGEX-2TK vector (Pharmacia, Uppsala, Sweden). The resulting cDNA construct contains a kinase recognition site at the amino terminus for radioactive labeling and glutathione S-transferase sequences at the carboxyl terminus for affinity purification (Nilsson, et al., *EMBO J.*, 4: 1075–80 (1985); Zabeau et al., *EMBO J.*, 1: 1217–24 (1982)).

In an insect system, Autographa californica nuclear polyhedrosis virus (AcNPV) is used as a vector to express foreign genes. The virus grows in *Spodoptera frugiperda* cells. The gene coding sequence may be cloned individually into non-essential regions (for example the polyhedrin gene) of the virus and placed under control of an AcNPV promoter (for example the polyhedrin promoter). Successful insertion of gene coding sequence will result in inactivation of the polyhedrin gene and production of non-occluded recombinant virus (ie., virus lacking the proteinaceous coat coded for by the polyhedrin gene). These recombinant viruses are then used to infect *Spodoptera frugiperda* cells in which the inserted gene is expressed (see, e.g., Smith, et al., *J. Virol.* 46: 584–93 (1983); U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing gene protein in infected hosts. (e.g., see Logan et al., *Proc. Natl. Acad. Sci. USA*, 81:3655–59 (1984)). Specific initiation signals may also be required for efficient translation of inserted gene coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter, et al., *Methods in Enzymol.*, 153:516–44 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines which stably express the gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells which stably integrate the plasmid into their chromosomes and grow, to form foci which in turn can be cloned and expanded into cell lines. This method may advantageously be used to engineer cell lines which express the gene protein. Such engineered cell lines may be particularly useful in screening and evaluation of compounds that affect the endogenous activity of the gene protein.

In a preferred embodiment, control of timing and/or quantity of expression of the recombinant protein can be controlled using an inducible expression construct. Inducible constructs and systems for inducible expression of recombinant proteins will be well known to those skilled in the art. Examples of such inducible promoters or other gene regulatory elements include, but are not limited to, tetracycline, metallothionine, ecdysone, and other steroid-responsive promoters, rapamycin responsive promoters, and the like (No, et al., *Proc. Natl. Acad. Sci. USA*, 93:3346–51 (1996); Furth, et al., *Proc. Natl. Acad. Sci. USA*, 91:9302–6 (1994)). Additional control elements that can be used include promoters requiring specific transcription factors such as viral, particularly HIV, promoters. In one in embodiment, a Tet inducible gene expression system is utilized. (Gossen et al., *Proc. Natl. Acad. Sci. USA*, 89:5547–51 (1992); Gossen, et al., *Science*, 268:1766–69 (1995)). Tet Expression Systems are based on two regulatory elements derived from the tetracycline-resistance operon of the *E. coli* Tn10 transposon—the tetracycline repressor protein (TetR) and the tetracycline operator sequence (tetO) to which TetR binds. Using such a system, expression of the recombinant protein is placed under the control of the tetO operator sequence and transfected or transformed into a host cell. In the presence of TetR, which is co-transfected into the host cell, expression of the recombinant protein is repressed due to binding of the TetR protein to the teto regulatory element. High-level, regulated gene expression can then be induced in response to varying concentrations of tetracycline (Tc) or Tc derivatives such as doxycycline (Dox), which compete with tetO elements for binding to TetR. Constructs and materials for tet inducible gene expression are available commercially from CLONTECH Laboratories, Inc., Palo Alto, Calif.

When used as a component in an assay system, the gene protein may be labeled, either directly or indirectly, to facilitate detection of a complex formed between the gene protein and a test substance. Any of a variety of suitable labeling systems may be used including but not limited to radioisotopes such as 125I; enzyme labeling systems that generate a detectable calorimetric signal or light when exposed to substrate; and fluorescent labels. Where recombinant DNA technology is used to produce the gene protein for such assay systems, it may be advantageous to engineer fusion proteins that can facilitate labeling, immobilization and/or detection.

Indirect labeling involves the use of a protein, such as a labeled antibody, which specifically binds to the gene product. Such antibodies include but are not limited to polyclonal, monoclonal, chimeric, single chain, Fab fragments and fragments produced by a Fab expression library.

Production of Antibodies

Described herein are methods for the production of antibodies capable of specifically recognizing one or more epitopes. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be used, for example, in the detection of a target gene in a biological sample, or, alternatively, as a method for the inhibition of abnormal target gene activity. Thus, such antibodies may be utilized as part of disease treatment methods, and/or may be used as part of diagnostic techniques whereby patients may be tested for abnormal levels of target gene proteins, or for the presence of abnormal forms of the such proteins.

For the production of antibodies, various host animals may be immunized by injection with the target gene, its expression product or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacille Calmette-Guerin*) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular an antigen, may be obtained by any technique which provides for the production of antibody molecules by continuous cell lines in culture. These include, but are not limited to the hybridoma technique of Kohler and Milstein, *Nature*, 256:495–7 (1975); and U.S. Pat. No. 4,376,110), the human B-cell hybridoma technique (Kosbor, et al., *Immunology Today*, 4:72 (1983); Cote, et al., *Proc. Natl. Acad. Sci. USA*, 80:2026–30 (1983)), and the EBV-hybridoma technique (Cole, et al., in Monoclonal Antibodies And Cancer Therapy, Alan R. Liss, Inc., New York, pp. 77–96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., *Proc. Natl. Acad. Sci.*, 81:6851–6855 (1984); Takeda, et al., *Nature*, 314:452–54 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–26 (1988); Huston, et al., *Proc. Natl. Acad. Sci. USA*, 85:5879–83 (1988); and Ward, et al., *Nature*, 334:544–46 (1989)) can be adapted to produce gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse, et al., *Science*, 246:1275–81 (1989)) to allow rapid and easy identification of monoclonal Fab fragments with the desired specificity.

Screening for Therapeutic Agents

Cells that contain and express target gene sequences may be used to screen for therapeutic agents. Such cells may include non-recombinant monocyte cell lines, such as U937 (ATCC#CRL-1593), THP-1 (ATCC#TIB-202), and P388D1 (ATCC#TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, such cells may include recombinant, transgenic cell lines. For example, the knockout mice of the invention may be used to generate cell lines, containing one or more cell types involved in a disease, that can be used as cell culture models for that disorder. While cells, tissues, and primary cultures derived from the disease transgenic animals of the invention may be utilized, the generation of continuous cell lines is preferred. For examples of techniques which may be used to derive a continuous cell line from the transgenic animals, see Small, et al., *Mol. Cell Biol.*, 5:642–48 (1985).

Target gene sequences may be introduced into, and overexpressed in, the genome of the cell of interest. In order to overexpress a target gene sequence, the coding portion of the target gene sequence may be ligated to a regulatory sequence which is capable of driving gene expression in the cell type of interest. Such regulatory regions will be well known to those of skill in the art, and may be utilized in the absence of undue experimentation. Target gene sequences may also be disrupted or underexpressed. Cells having target gene disruptions or underexpressed target gene sequences may be used, for example, to screen for agents capable of affecting alternative pathways which compensate for any loss of function attributable to the disruption or underexpression.

In vitro systems may be designed to identify compounds capable of binding the target gene products. Such compounds may include, but are not limited to, peptides made of D-and/or L-configuration amino acids (in, for example, the form of random peptide libraries; see e.g., Lam, et al., *Nature*, 354:82–4 (1991)), phosphopeptides (in, for example, the form of random or partially degenerate, directed phosphopeptide libraries; see, e.g., Songyang, et al., *Cell*, 72:767–78 (1993)), antibodies, and small organic or inorganic molecules. Compounds identified may be useful, for example, in modulating the activity of target gene proteins, preferably mutant target gene proteins; elaborating the biological function of the target gene protein; or screening for compounds that disrupt normal target gene interactions or themselves disrupt such interactions.

The principle of the assays used to identify compounds that bind to the target gene protein involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the target gene protein or the test substance onto a solid phase and detecting target protein/test substance complexes anchored on the solid phase at the end of the reaction. In one embodiment of such a method, the target gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Compounds that are shown to bind to a particular target gene product through one of the methods described above can be further tested for their ability to elicit a biochemical response from the target gene protein. Agonists, antagonists and/or inhibitors of the expression product can be identified utilizing assays well known in the art.

Antisense, Ribozymes, and Antibodies

Other agents which may be used as therapeutics include the target gene, its expression product(s) and functional fragments thereof. Additionally, agents which reduce or inhibit mutant target gene activity may be used to ameliorate disease symptoms. Such agents include antisense, ribozyme, and triple helix molecules. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant target gene alleles. In order to ensure that substantially normal levels of target gene activity are maintained, nucleic acid molecules that encode and express target gene polypeptides exhibiting normal activity may be introduced into cells that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2'-O-methyl rather than phosphodiesterase linkages within the oligodeoxyribonucleotide backbone.

Antibodies that are both specific for target gene protein, and in particular, mutant gene protein, and interfere with its activity may be used to inhibit mutant target gene function. Such antibodies may be generated against the proteins themselves or against peptides corresponding to portions of the proteins using standard techniques known in the art and as also described herein. Such antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin liposomes may be used to deliver the antibody or a fragment of the Fab region which binds to the target gene epitope into cells. Where fragments of the antibody are used, the smallest inhibitory fragment which binds to the target or expanded target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (see, e.g., Creighton, Proteins: Structures and Molecular Principles (1984) W. H. Freeman, New York 1983, supra; and Sambrook, et al., 1989, supra). Alternatively, single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco, et al., *Proc. Natl. Acad. Sci. USA*, 90:7889–93 (1993).

RNA sequences encoding target gene protein may be directly administered to a patient exhibiting disease symptoms, at a concentration sufficient to produce a level of target gene protein such that disease symptoms are ameliorated. Patients may be treated by gene replacement therapy. One or more copies of a normal target gene, or a portion of the gene that directs the production of a normal target gene protein with target gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of disease symptoms.

Pharmaceutical Compositions, Effective Dosages, and Routes of Administration

The identified compounds that inhibit target mutant gene expression, synthesis and/or activity can be administered to a patient at therapeutically effective doses to treat or ameliorate the disease. A therapeutically effective dose refers to that amount of the compound sufficient to result in amelioration of symptoms of the disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, topical, subcutaneous, intraperitoneal, intravenous, intrapleural, intraoccular, intraarterial, or rectal administration. It is also contemplated that pharmaceutical compositions may be administered with other products that potentiate the activity of the compound and optionally, may include other therapeutic ingredients.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or . retention enemas, e.g., containing conventional suppository bases such as cocoa butter or other glycerides. Oral ingestion is possibly the easiest method of taking any medication. Such a route of administration, is generally simple and straightforward and is frequently the least inconvenient or unpleasant route of administration from the patient's point of view. However, this involves passing the material through the stomach, which is a hostile environment for many materials, including proteins and other biologically active compositions. As the acidic, hydrolytic and proteolytic environment of the stomach has evolved efficiently, to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine. The result, is that many proteinaceous medicaments must be taken in through another method, such as parenterally, often by subcutaneous, intramuscular or intravenous injection.

Pharmaceutical compositions may also include various buffers (e.g., Tris, acetate, phosphate), solubilizers (e.g., Tween, Polysorbate), carriers such as human serum albumin, preservatives (thimerosol, benzyl alcohol) and anti-oxidants such as ascorbic acid in order to stabilize pharmaceutical activity. The stabilizing agent may be a detergent, such as tween-20, tween-80, NP-40 or Triton X-100. EBP may also be incorporated into particulate preparations of polymeric compounds for controlled delivery to a patient over an extended period of time. A more extensive survey of components in pharmaceutical compositions is found in Remington's Pharmaceutical Sciences, 18th ed., A. R. Gennaro, ed., Mack Publishing, Easton, Pa. (1990).

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostics

A variety of methods may be employed to diagnose disease conditions associated with the target gene. Specifically, reagents may be used, for example, for the detection of the presence of target gene mutations, or the detection of either over or under expression of target gene mRNA.

According to the diagnostic and prognostic method of the present invention, alteration of the wild-type target gene locus is detected. In addition, the method can be performed by detecting the wild-type target gene locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are mutated, then a late neoplastic state may be indicated. The finding of gene mutations thus provides both diagnostic and prognostic information. A target gene allele which is not deleted (e.g., that found on the sister chromosome to a chromosome carrying a target gene deletion) can be screened for other mutations, such as insertions, small deletions, and point mutations. Mutations found in tumor tissues may be linked to decreased expression of the target gene product. However, mutations leading to non-functional gene products may also be linked to a cancerous state. Point mutational events may occur in regulatory regions, such as in the promoter of the gene, leading to loss or diminution of expression of the mRNA. Point mutations may also abolish proper RNA processing, leading to loss of expression of the target gene product, or a decrease in mRNA stability or translation efficiency.

One test available for detecting mutations in a candidate locus is to directly compare genomic target sequences from cancer patients with those from a control population. Alternatively, one could sequence messenger RNA after amplification, e.g., by PCR, thereby eliminating the necessity of determining the exon structure of the candidate gene. Mutations from cancer patients falling outside the coding region of the target gene can be detected by examining the non-coding regions, such as introns and regulatory sequences near or within the target gene. An early indication that mutations in noncoding regions are important may come from Northern blot experiments that reveal messenger RNA molecules of abnormal size or abundance in cancer patients as compared to control individuals.

The methods described herein may be performed, for example, by utilizing pre-packaged diagnostic kits comprising at least one specific gene nucleic acid or anti-gene antibody reagent described herein, which may be conveniently used, e.g., in clinical settings, to diagnose patients exhibiting disease symptoms or at risk for developing disease.

Any cell type or tissue, preferably monocytes, endothelial cells, or smooth muscle cells, in which the gene is expressed may be utilized in the diagnostics described below.

DNA or RNA from the cell type or tissue to be analyzed may easily be isolated using procedures which are well known to those in the art. Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR In Situ Hybridization: Protocols and Applications, Raven Press, N.Y. (1992)).

Gene nucleotide sequences, either RNA or DNA, may, for example, be used in hybridization or amplification assays of biological samples to detect disease-related gene structures and expression. Such assays may include, but are not limited to, Southern or Northern analyses, restriction fragment length polymorphism assays, single stranded conformational polymorphism analyses, in situ hybridization assays, and polymerase chain reaction analyses. Such analyses may reveal both quantitative aspects of the expression pattern of the gene, and qualitative aspects of the gene expression and/or gene composition. That is, such aspects may include, for example, point mutations, insertions, deletions, chromosomal rearrangements, and/or activation or inactivation of gene expression.

Preferred diagnostic methods for the detection of gene-specific nucleic acid molecules may involve for example, contacting and incubating nucleic acids, derived from the cell type or tissue being analyzed, with one or more labeled nucleic acid reagents under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue which have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art.

Alternative diagnostic methods for the detection of gene-specific nucleic acid molecules may involve their amplification, e.g., by PCR (the experimental embodiment set forth in Mullis U.S. Pat. No. 4,683,202 (1987)), ligase chain reaction (Barany, Proc. Natl. Acad. Sci. USA, 88:189–93 (1991)), self sustained sequence replication (Guatelli, et al., Proc. Natl. Acad. Sci. USA, 87:1874–78 (1990)), transcriptional amplification system (Kwoh, et al., Proc. Natl. Acad. Sci. USA, 86:1173–77 (1989)), Q-Beta Replicase (Lizardi et al., Bio/Technology, 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to monocytes, endothelium, and/or smooth muscle. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method may be chosen from among the gene nucleic acid reagents described herein. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Antibodies directed against wild type or mutant gene peptides may also be used as disease diagnostics and prognostics. Such diagnostic methods, may be used to detect abnormalities in the level of gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques which are well known to those of skill in the art, including but not limited to western blot analysis. For a detailed explanation of methods for carrying out western blot analysis, see Sambrook, et al. (1989) supra, at Chapter 18. The protein detection and isolation methods employed herein may also be such as those described in Harlow and Lane, for example, (Antibodies: A Laboratory Manual, Cold Spring Harbor Laboratory Press, Cold Spring Harbor, N.Y. (1988)).

Preferred diagnostic methods for the detection of wild type or mutant gene peptide molecules may involve, for example, immunoassays wherein fingerprint gene peptides are detected by their interaction with an anti-fingerprint gene-specific peptide antibody.

For example, antibodies, or fragments of antibodies useful in the present invention may be used to quantitatively or qualitatively detect the presence of wild type or mutant gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Imunoassays for wild type, mutant, or expanded fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled gene-specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those 'skilled in the an will know many other suitable carriers for binding antibody or antigen, or will be able to ascertain the same by use of routine experimentation.

The binding activity of a given lot of anti-wild type or -mutant fingerprint gene peptide antibody may be determined according to well known methods. Those skilled in the art will be able to determine operative and optimal assay conditions for each determination by employing routine experimentation.

One of the ways in which the gene peptide-specific antibody can be detectably labeled is by linking the same to an enzyme and using it in an enzyme immunoassay (EIA) (Voller, *Ric Clin Lab,* 8:289–98 (1978) ["The Enzyme Linked Immunosorbent Assay (ELISA)", Diagnostic Horizons 2:1–7, 1978, Microbiological Associates Quarterly Publication, Walkersville, Md.]; Voller, et al., *J. Clin. Pathol.,* 31:507–20 (1978); Butler, *Meth. Enzymol.,* 73:482–523 (1981); Maggio (ed.), Enzyme Immunoassay, CRC Press, Boca Raton, Fla. (1980); Ishikawa, et al., (eds.) Enzyme Immunoassay, lgaku-Shoin, Tokyo (1981)). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type, mutant, or expanded peptides through the use of a radioimmunoassay (RIA) (see, e.g., Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Throughout this application, various publications, patents and published patent applications are referred to by an identifying citation. The disclosures of these publications, patents and published patent specifications referenced in this application are hereby incorporated by reference into the present disclosure to more fully describe the state of the art to which this invention pertains.

The following examples are intended only to illustrate the present invention and should in no way be construed as limiting the subject invention.

EXAMPLES

Example 1

Direct Construct Construction from a Plasmid Library

Genomic libraries using the lambda ZAP™ system were prepared as follows. Embryonic stem cells were grown in 100 mm tissue culture plates. High molecular weight genomic DNA was isolated from these ES cells by adding 5 ml of lysis buffer (10 mM Tris-HCL pH7.5, 10 mM EDTA pH 8.0, 10 mM NaCl, 0.5% SDS, and 1 mg/ml Proteinase K) to a confluent 100 mm plate of embryonic stem cells. The cells were then incubated at 60° C. for several hours or until fully lysed. Genomic DNA was purified from the lysed cells by several rounds of gentle phenol:chloroform extractions followed by ethanol precipitation.

The genomic DNA was partially digested with the restriction enzyme Sau 3A I to generate fragments of approximately 5–20 kb. The ends of these fragments were partially filled in by addition of DATP and dGTP in the present of Klenow DNA polymerase, creating incompatible ends on the genomic fragments. Size fragments of between 5 and 10 kb were then purified by agarose gel electrophoresis (1×TAE, 0.8% gel). The DNA was then isolated from the excised agarose pieces using a QIAquick gel extraction kit (Qiagen, Inc., Valencia, Calif.).

The genomic fragments were ligated into the Lambda Zap™ II vector (Stratagene, Inc., La Jolla, Calif.) that had been cut with Xho I and partially filled in using dTTP, dCTP, and Klenow DNA polymerase. After ligation, the DNA was packaged using a lambda packaging mix (Gigapack m gold, Stratagene, Inc., La Jolla, Calif.) and the titer was determined.

Circular phagemid DNA was derived from the lambda library by growing the lambda clones on the appropriate bacterial strain (XL-1 Blue MRF[1], Stratagene, Inc.) in the presence of the M13 helper phage, ExAssist (Stratagene, Inc.). Specifically, approximately 100,000 lambda clones were incubated with a 10–100 fold excess of both bacteria and helper phage for 20 minutes at 37° C. One ml of LB media +10 mM MgSO$_4$ was added to each excision reaction and it was incubated overnight at 37° C. with shaking. Typically 24–96 of these reactions were set up at a time in a 96 well deep-well block. The following morning, the block was heated to 65° C. for 15 minutes to kill both the bacteria and the lambda phage. Bacterial debris was removed by centrifugation at approximately 3000 g for 15 minutes. The supernatant containing the circular phagemid DNA, was retained and used directly in plasmid PCR.

The pools of phagemid DNA described above were screened for specific genes of interest using long-range PCR and "outward pointing" oligos, chosen as described above based on the known sequence (depicted in FIG. 1). The PCR reactions contains 2 μl of a pool phagemid DNA sample, 3 μl of 10×PCR Buffer 3 (Boehringer Mannheim), 1.1 μl 10 mM dNTPs, 50 nM primers, 0.3 μl of EXPAND Long Template PCR Enzyme Mix (Boehringer-Mannheim) and 30 μl of H$_2$0. Cycling conditions were 94° C. for 2 minutes (1 cycle); 94° C. for 10 seconds, 65° C. for 30 seconds, 68° C. for 15 seconds (15 cycles); 94° C. for 10 seconds, 60° C. for 30 seconds, 68° C for 15 seconds plus 20 seconds increase per each additional cycle (25 cycles); 68° C. for 7 minutes (1 cycle) and holding at 4° C.

The products of the PCR reactions were separated by electrophoresis through agarose gels containing 1×TAE buffer and visualized with ethidium bromide and UV light. Any large fragments indicative of successful long-range PCR were excised from the gel and purified using QIAquick PCR purification kit (Qiagen).

In order to eliminate the need to restriction map the PCR fragments, the following ligation-independent cloning strategy was employed. The long-range PCR fragment of interest was "purified" using a QlAquick PCR purification kit (Qiagen, Inc., Santa Clarita, Calif.). Single-stranded ends of the PCR fragments were generated by mixing: 0.1–2 μg of the fragment; 2 μl of NEB (New England BioLabs) Buffer 4; 1 μl of 2 mM dTTP, 6 units of T4 DNA polymerase (NEB), H$_2$O to total volume of 20 μl and incubating at 25° C. for 30 minutes. The polymerase was inactivated by heating at 75° C. for 20 minutes. Single-stranded ends were also created on the Neo$^r$ selectable marker fragment by digesting the plasmid vector pDG2 at the unique restriction sites, with Sac I and Sac II (pDG2 depicted in FIG. 2A) and treating each reaction with T4 DNA polymerase as above. The vector shown in FIG. 1 was prepared with single-stranded ends complementary to those on the long-range PCR fragment.

The vector and fragments were then assembled into constructs using either a two-step cloning strategy or a four-way, single-step protocol. Briefly, a reaction containing 10 ng of T4-treated Neo$^r$ cassette, 1 μl of T4-treated PCR fragment, 0.2 μl of 0.5 M EDTA, 0.3 μl of 0.5 M NaCl and H$_2$O up to 4 μl was heated to 65° C. and allowed to cool to room temperature over approximately 45 minutes. The mixture was then transformed into subcloning efficiency DH5-αcompetent cells.

Example 2

Generation of Constructs from Phage Libraries

A mouse embryonic stem cell library was prepared in lambda phage as follows. Genomic libraries were constructed from genomic DNA by partial cleavage of DNA at Sau 3AI sites to yield genomic fragments of approximately 20 kb in length. The terminal sequences of these DNA fragments were partially filled in using Klenow enzyme in the presence of dGTP and dATP and the fragments were ligated using T4 DNA ligase into Xho I sites of an appropriate lambda cloning vector, e.g., lambda Fix II (Stratagene, Inc., La Jolla, Calif.), which had been partially filled in using Klenow in the presence of dilt and dCTP. Alternatively, the partially digested genomic DNA was size selected using a sucrose gradient and sequences of approximately 20 kb selected for. The enriched fraction was cloned into a Bam HI cut lambda vector, e.g., lambda Datsh II (Stratagene, Inc., La Jolla, Calif.).

The library was plated onto 1,152 plates, each plate containing approximately 1,000 clones. Thus, a total of 1.1 million clones (the equivalent of 8 genomes) was plated.

The phage were eluted from each plate by adding 4 ml of lambda elution buffer (10 mM MgCl$_2$, 10 mM Tris-pH 8.0)

to each plate and incubating for 3 to 5 hours at room temperature. After incubation, 2 ml of buffer was collected from each plate and placed into one well of a 96 deep well plate (Costar, In.). Twelve 96-well plates were filled and referred to as the "sub-pool library."

Using the sub-pool library, "pool libraries" were made by placing 100 µl of 12 different subpool wells into one well of a new 96 well plate. The 12 sub-pool plates were combined to form 1 plate of pool libraries.

Using a pair of oligonucleotides that were known to PCR-amplify the gene of interest, supernatant from the 96 pools of the "large-pool library" were amplified. PCR was performed in the presence of 0.5 units of Amplitaq Gold™ (Perkin Elmer), 1 µM of each oligonucleotide, 200 µM dNTPs, 2 µl of a 1 to 5 dilution of the pool (or subpool) supernatant, 50 mM KCl, 100 mM Tris-HCl (pH 8.3), and either 1.5 mM or 1.25 mM $MgCl_2$. Cycling conditions were 95° C. for 8 minutes (1 cycle); 95° C. for 30 seconds, 60° C. for 30 seconds, 72° C. for 45 seconds (55 cycles); 72° C. for 7 minutes (1 cycle) and holding at 4° C. Depending on the gene, between about 3 and 12 pool yielded positive signals as identified on agarose gels as described in Example 1. In cases where further purification was necessary (i.e. where a clear signal was not present after amplification), the 12 sub-pools making up the pool were subjected to amplification using the same primers and a single sub-pool (1000 clones) was identified.

Generation of Flanking Fragments

As described above, knock-out constructs contain two blocks of DNA sequence homologous to the target gene, flanking a positive selection marker. Long-range PCR was performed from the pools of lambda clones positively identified as described above in Example 2. Each fragment was generated using a pair of oligonucleotides with predetermined sequences lacking one type of base and complementary to predetermined sequences on the vector. The fragments obtained were between 1 and 5 kb. A third fragment, longer than 5 kb, is also generated using appropriate oligonucleotides. This third fragment was then used to obtain DNA sequences near the gene to be knocked out but outside of the vector.

Example 3

Two-Step Cloning—General Procedure

The pDG2 plasmid vector (FIG. 2A) contains unique restriction sites Sac II and Sac I. Appropriate single-stranded annealing sites were generated by digesting the pDG2 vector with either restriction enzyme Sac II or Sac I and treating each reaction with T4 DNA polymerase and dTTP as described above. Four reactions were set up in microtitre plates for each vector, the reaction containing 1 µl of either (1) T4 DNA polymerase-treated fragments; (2) a 1:10 dilution of the T4-treated fragments reaction; (3) a 1:100 dilution of the T4-treated fragments or (4) $H_2O$ (no insert control). The microtitre plates were sealed, placed in-between two temperature blocks heated to 65° C., and allowed to cool slowly at room temperature for 30 to 45 minutes.

The microtitre plate was then placed on ice and 20–25 µl of subcloning efficiency competent cells added to each well. The plate was incubated on ice for 20–30 minutes. The microtitre plate was then placed between two temperature blocks heated to 42° C. for 2 minutes, followed by 2 minutes on ice. 100 µl of LB was added to each well, the plate covered with parafilm and incubated 30–60 minutes at 37° C. The entire contents of each well were plated on one LB-Amp plate and incubated at 37° C. overnight.

Between about 12–24 colonies were picked from plates which had at least 2–4 times more colonies than the no insert control. The colonies were grown in deep well plates overnight at 37° C. and then the plasmid DNA extracted using a Qiagen mini-prep kit.

Figure 2A:
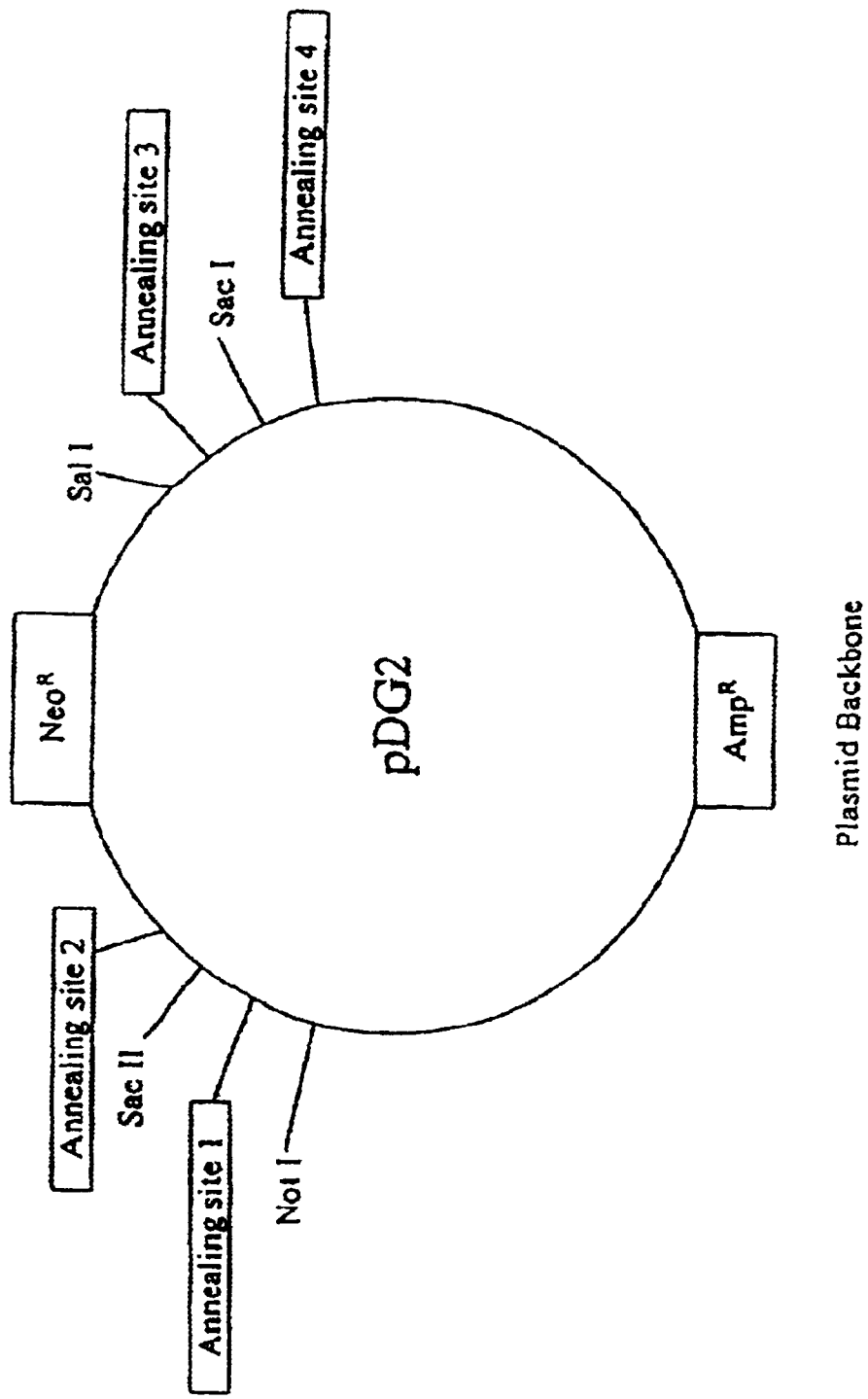
FIG. 2A is a schematic depicting the pDG2 vector. The vector contains an ampicillin resistance gene and a neomycin (Neo$^r$) gene. On each side of the Neo$^r$ gene are two sites for ligation-independent cloning along with restriction sites. The sequence of pDG2 is shown in FIG. 2B and SEQ ID NO:1.

The plasmid DNA.was digested with Not I and Sal I enzymes. As shown in FIG. 2A, a Not I/Sal I digestion will generate a large fragment containing cloning sites 3 and 4 and a smaller fragment containing cloning sites 1 and 2 and the $Neo^r$ gene. After digestion, the reactions were run on a 0.8% agarose gel containing 0.2 µg/ml ethidium bromide. For no inserts, two bands were present, one of 1975 base pairs and one of 2793 base pairs. When an insert fragment was present, at, least one of these bands would be larger because it would also contain a fragment (insert 1 or 2) either at the annealing site 1/2 or the site 3/4. The insert bands were excised and treated with a QIAquick gel extraction kit. A second ligation reaction was performed containing 1 µl of 10× ligase buffer (50 mM Tris-HCl pH 7.5, 10 mM $MgCl_2$, 10 mM dithiothreitol, 1 mM ATP, 25 µg/ml bovine serum albumin), 1 µl T4 DNA ligase, 1–2 µl fragment (site 3/4 band), 5 µl of site 1/2 band and $H_2O$ up to 10 µl. Controls were also set up replacing either the site 3/4 fragment or the site 1/2 fragment with water. The reactions were incubated 1 to 2 hours at room temperature and transformed with 25 µl of competent cells.

"Flanking DNA" in the context of these examples refers to the genomic sequences flanking the region in the target gene that is to be deleted or mutated. "Flanking DNA" is also described above as the blocks of DNA sequence homologous to the target gene. R1 genomic library refers to a genomic library prepared from the R1 ES cell line. Such libraries can be prepared such as described in Example 1.

Example 4

Generation and Analysis of Mice Comprising Retina—Specific Nuclear Receptor Gene Disruptions To investigate the role of retina-specific nuclear receptors, disruptions in retina-specific nuclear receptor genes were produced by homologous recombination. Specifically, transgenic mice comprising disruptions in retina-specific nuclear receptor genes were created. More particularly, a retina-specific targeting construct having the ability to disrupt or modify retina-specific nuclear receptor genes, specifically comprising SEQ ID NO:19 was created using the oligonucleotide sequences identified herein as SEQ ID NO:20 or SEQ ID NO:21. The targeting construct was introduced into ES cells derived from the 129/Sv−+P+Mgf-SLJ/J mouse substrain to generate chimeric mice. F1 mice were generated by breeding with C57B116 females. F2 homozygous mutant mice were produced by intercrossing F1 heterozygous males and females. The transgenic animals comprising disruptions in retina-specific nuclear receptor genes were analyzed for phenotypic changes and expression patterns. The phenotypes associated with a disruption in a retina-specific nuclear receptor gene were determined as follows:

Homozygous Mice:

The homozygous mice analyzed demonstrated at least one of the following phenotypes:

Eyes

Eye abnormalities, including severe retinal dysplasia characterized by extensive rosette formation and retinal folding; segmental thinning of the outer nuclear layer of the retina with rods and cones filling the foci; and complete unilateral absence of the retina. Moreover, the space normally occupied by the retina was filled with fibrous connective tissue, spicules of osteoid and some mineral. In areas, connective tissue was adherent to the posterior lens capsule. Posterior synechia with a thickened iris adherent to the anterior aspect of the lens was detected. The pigmented epithelial layer of the retina was thickened and its cells were increased in size and number. The internal structure of the lens was disorganized and comprised swollen and degenerated fibers. In instances where the retina was absent unilaterally, small focal remnants were present.

Gastrointestinal Tract

Abnormalities in the gastrointestinal tract included multifocal infiltrates of neutrophils in the deep mucosa and submucosa in the stomach.

Skin

Abnormalities in the skin included focal lymphocytic inflammation within the dermis.

Testes/Epididymides

Abnormalities in the testes and epididymides included reduced spermatogenesis. Specifically, seminiferous tubules had scattered degenerate or necrotic spermatogenetic epithelial cells and multinucleated giant cells. The epididymides had reduced number of sperinatids, and degenerated cells were present in tubules. The epithelial cells of some epididymal tubules were vacuolated.

Clinical Chemistry/BloodAnalysis

Abnormalities included low alanine aminotransferase (ALT) values, aspartate aminotransferase (AST), and creatinine kinase (CK) values as compared to wild-type control values. Alkaline phosphatase (ALP) activity, however, was elevated. Hematological evaluation showed lower total white blood cell count.

Heterozygous Mice

Skin

Abnormalities included local fibrosis and lymphocytic dermatitis.

Liver

Abnormalities included pericholangitis with bile duct hyperplasia and fibrosis.

As is apparent to one of skill in the art, various modifications of the above embodiments can be made without departing from the spirit and scope of this invention. These modifications and variations are within the scope of this invention.

What is claimed is:

1. A transgenic mouse comprising a heterozygous disruption in a retina-specific nuclear receptor gene, wherein said disruption in a homozygous state inhibits production of a functional retina-specific nuclear receptor protein resulting in a transgenic mouse exhibiting an eye abnormality.

2. A transgenic mouse whose genome comprises a homozygous disruption in an endogenous retina-specific nuclear receptor gene, wherein the transgenic mouse lacks production of functional retina-specific nuclear receptor and exhibits an eye abnormality.

3. The transgenic mouse of claim 2, wherein the eye abnormality is retinal dysplasia.

4. A cell or tissue isolated from the transgenic mouse of claim 2.

5. A method of producing a transgenic mouse comprising a disruption in an endogenous retina-specific nuclear receptor gene, the method comprising:

(a) introducing a targeting vector which disrupts the endogenous retina-specific nuclear receptor gene in a mouse embryonic stem cell;

(b) selecting the embryonic stem cell whose genome comprises disrupted retina-specific nuclear receptor gene;

(c) introducing the embryonic stem cell of step (b) into a blastocyst;

(d) implanting the resulting blastocyst into a pseudopregnant mouse, wherein said pseudopregnant mouse gives birth to a chimeric mouse;

(d) breeding the chimeric mouse to produce the transgenic mouse comprising a heterozygous disruption in the retina-specific nuclear receptor gene; and (e) breeding the transgenic mouse of step (d) to produce a trans genic mouse whose genome comprises a homozygous disruption of the retina-specific nuclear receptor gene such that the mouse lacks production of functional retina-specific nuclear receptor and exhibits an eye abnormality.

6. The method of claim 5, wherein the eye abnormality is retinal dysplasia.

* * * * *

SEQUENCE LISTING

<160> NUMBER OF SEQ ID NOS: 21

<210> SEQ ID NO 1
<211> LENGTH: 4768
<212> TYPE: DNA
<213> ORGANISM: Artificial Sequence
<220> FEATURE:
<223> OTHER INFORMATION: Phage Vector

<400> SEQUENCE: 1

```
gttaactacg tcaggtggca cttttcgggg aaatgtgcgc ggaaccccta tttgtttatt      60
tttctaaata cattcaaata tgtatccgct catgagacaa taaccctgat aaatgcttca     120
ataatattga aaaggaaga gtatgagtat tcaacatttc cgtgtcgccc ttattccctt     180
ttttgcggca ttttgccttc ctgttttgc tcacccagaa acgctggtga agtaaaaga     240 tgctgaagat cagttgggtg cacgagtggg ttacatcgaa ctggatctca acagcggtaa     300
gatccttgag agttttcgcc ccgaagaacg ttctccaatg atgagcactt ttaaagttct     360
gctatgtggc gcggtattat cccgtgttga cgccgggcaa gagcaactcg gtcgccgcat     420
acactattct cagaatgact tggttgagta ctcaccagtc acagaaaagc atcttacgga     480
tggcatgaca gtaagagaat tatgcagtgc tgccataacc atgagtgata acactgcggc     540
caacttactt ctgacaacga tcggaggacc gaaggagcta accgcttttt tgcacaacat     600
gggggatcat gtaactcgcc ttgatcgttg ggaaccggag ctgaatgaag ccataccaaa     660
cgacgagcgt gacaccacga tgcctgtagc aatggcaaca acgttgcgca aactattaac     720
tggcgaacta cttactctag cttcccggca acaattaata gactggatgg aggcggataa     780
```

-continued

| | | | | |
|---|---|---|---|---|
| agttgcagga | ccacttctgc | gctcggccct | tccggctggc | tggtttattg | ctgataaatc | 840 |
| tggagccggt | gagcgtgggt | ctcgcggtat | cattgcagca | ctgggccag | atggtaagcc | 900 |
| ctcccgtatc | gtagttatct | acacgacggg | gagtcaggca | actatggatg | aacgaaatag | 960 |
| acagatcgct | gagataggtg | cctcactgat | taagcattgg | taactgtcag | accaagttta | 1020 |
| ctcatatata | ctttagattg | atttaccccg | gttgataatc | agaaaagccc | caaaacagg | 1080 |
| aagattgtat | aagcaaatat | ttaaattgta | aacgttaata | ttttgttaaa | attcgcgtta | 1140 |
| aattttgtt | aaatcagctc | attttttaac | caataggccg | aaatcggcaa | aatcccttat | 1200 |
| aaatcaaaag | aatagcccga | gatagggttg | agtgttgttc | cagtttggaa | caagagtcca | 1260 |
| ctattaaaga | acgtggactc | caacgtcaaa | gggcgaaaaa | ccgtctatca | gggcgatggc | 1320 |
| ccactacgtg | aaccatcacc | caaatcaagt | tttttgggt | cgaggtgccg | taaagcacta | 1380 |
| aatcggaacc | ctaaagggag | cccccgattt | agagcttgac | ggggaaagcg | aacgtggcga | 1440 |
| gaaaggaagg | gaagaaagcg | aaaggagcgg | gcgctagggc | gctggcaagt | gtagcggtca | 1500 |
| cgctgcgcgt | aaccaccaca | cccgccgcgc | ttaatgcgcc | gctacagggc | gcgtaaaagg | 1560 |
| atctaggtga | agatcctttt | tgataatctc | atgaccaaaa | tcccttaacg | tgagttttcg | 1620 |
| ttccactgag | cgtcagaccc | cgtagaaaag | atcaaaggat | cttcttgaga | tcctttttt | 1680 |
| ctgcgcgtaa | tctgctgctt | gcaaacaaaa | aaaccaccgc | taccagcggt | ggtttgtttg | 1740 |
| ccggatcaag | agctaccaac | tcttttccg | aaggtaactg | gcttcagcag | agcgcagata | 1800 |
| ccaaatactg | ttcttctagt | gtagccgtag | ttaggccacc | acttcaagaa | ctctgtagca | 1860 |
| ccgcctacat | acctcgctct | gctaatcctg | ttaccagtgg | ctgctgccag | tggcgataag | 1920 |
| tcgtgtctta | ccgggttgga | ctcaagacga | tagttaccgg | ataaggcgca | gcggtcgggc | 1980 |
| tgaacggggg | gttcgtgcac | acagcccagc | ttggagcgaa | cgacctacac | cgaactgaga | 2040 |
| tacctacagc | gtgagctatg | agaaagcgcc | acgcttcccg | aagggagaaa | ggcggacagg | 2100 |
| tatccggtaa | gcggcagggt | cggaacagga | gagcgcacga | gggagcttcc | agggggaaac | 2160 |
| gcctggtatc | tttatagtcc | tgtcgggttt | cgccacctct | gacttgagcg | tcgatttttg | 2220 |
| tgatgctcgt | caggggggcg | gagcctatgg | aaaaacgcca | gcaacgcggc | ctttttacgg | 2280 |
| ttcctggcct | tttgctggcc | ttttgctcac | atgtaatgtg | agttagctca | ctcattaggc | 2340 |
| accccaggct | ttacactta | tgcttccggc | tcgtatgttg | tgtggaattg | tgagcggata | 2400 |
| acaatttcac | acaggaaaca | gctatgacca | tgattacgcc | aagctacgta | atacgactca | 2460 |
| ctaggcggcc | gcgtttaaac | aatgtgctcc | tctttggctt | gcttccgcgg | gccaagccag | 2520 |
| acaagaacca | gttgacgtca | agcttcccgg | gacgcgtgct | agcggcgcgc | cgaattcctg | 2580 |
| caggattcga | gggcccctgc | aggtcaattc | taccgggtag | gggaggcgct | tttcccaagg | 2640 |
| cagtctggag | catgcgcttt | agcagccccg | ctggcacttg | gcgctacaca | agtggcctct | 2700 |
| ggcctcgcac | acattccaca | tccaccggta | gcgccaaccg | gctccgttct | ttggtggccc | 2760 |
| cttcgcgcca | ccttctactc | ctcccctagt | caggaagttc | cccccgccc | cgcagctcgc | 2820 |
| gtcgtgcagg | acgtgacaaa | tggaagtagc | acgtctcact | agtctcgtgc | agatggacag | 2880 |
| caccgctgag | caatggaagc | gggtaggcct | ttggggcagc | ggccaatagc | agctttgctc | 2940 |
| cttcgctttc | tgggctcaga | ggctgggaag | ggtgggtcc | ggggcgggc | tcaggggcgg | 3000 |
| gctcaggggc | gggcgggcg | cgaaggtcct | cccgaggccc | ggcattctcg | cacgcttcaa | 3060 |
| aagcgcacgt | ctgccgcgct | gttctcctct | tcctcatctc | cgggcctttc | gacctgcagc | 3120 |
| caatatggga | tcggccattg | aacaagatgg | attgcacgca | ggttctccgg | ccgcttgggt | 3180 |

-continued

```
ggagaggcta ttcggctatg actgggcaca acagacaatc ggctgctctg atgccgccgt    3240
gttccggctg tcagcgcagg ggcgcccggt tcttttttgtc aagaccgacc tgtccggtgc    3300
cctgaatgaa ctgcaggacg aggcagcgcg gctatcgtgg ctggccacga cgggcgttcc    3360
ttgcgcagct gtgctcgacg ttgtcactga agcgggaagg gactggctgc tattgggcga    3420
agtgccgggg caggatctcc tgtcatctca ccttgctcct gccgagaaag tatccatcat    3480
ggctgatgca atgcggcggc tgcatacgct tgatccggct acctgcccat tcgaccacca    3540
agcgaaacat cgcatcgagc gagcacgtac tcggatggaa gccggtcttg tcgatcagga    3600
tgatctggac gaagagcatc aggggctcgc gccagccgaa ctgttcgcca ggctcaaggc    3660
gcgcatgccc gacggcgatg atctcgtcgt gacccatggc gatgcctgct tgccgaatat    3720
catggtggaa aatggccgct tttctggatt catcgactgt ggccggctgg gtgtggcgga    3780
ccgctatcag gacatagcgt tggctacccg tgatattgct gaagagcttg gcggcgaatg    3840
ggctgaccgc ttcctcgtgc tttacggtat cgccgctccc gattcgcagc gcatcgcctt    3900
ctatcgcctt cttgacgagt tcttctgagg ggatcgatcc gtcctgtaag tctgcagaaa    3960
ttgatgatct attaaacaat aaagatgtcc actaaaatgg aagttttttcc tgtcatactt    4020 tgttaagaag ggtgagaaca gagtacctac attttgaatg gaaggattgg agctacgggg    4080 gtggggggtgg ggtgggatta gataaatgcc tgctctttac tgaaggctct ttactattgc    4140
tttatgataa tgtttcatag ttggatatca taatttaaac aagcaaaacc aaattaaggg    4200
ccagctcatt cctcccactc atgatctata gatctataga tctctcgtgg gatcattgtt    4260
tttctcttga ttcccacttt gtggttctaa gtactgtggt ttccaaatgt gtcagtttca    4320
tagcctgaag aacgagatca gcagcctctg ttccacatac acttcattct cagtattgtt    4380
ttgccaagtt ctaattccat cagaagctga ctctagatct ggatccggcc agctaggccg    4440
tcgacctcga gtgatcaggt accaaggtcc tcgctctgtg tccgttgagc tcgacgacac    4500
aggacacgca aattaattaa ggccggcccg taccctctag tcaaggcctt aagtgagtcg    4560
tattacggac tggccgtcgt tttacaacgt cgtgactggg aaaaccctgg cgttacccaa    4620
cttaatcgcc ttgcagcaca tcccccttttc gccagctggc gtaatagcga agaggcccgc    4680
accgatcgcc cttcccaaca gttgcgcagc ctgaatggcg aatggcgctt cgcttggtaa    4740
taaagcccgc ttcggcgggc tttttttt                                      4768
```

<210> SEQ ID NO 2
<211> LENGTH: 6355
<212> TYPE: DNA
<213> ORGANISM: Artificial Sequence
<220> FEATURE:
<223> OTHER INFORMATION: Phage Vector

<400> SEQUENCE: 2

```
gtttaatagt aatcaattac ggggtcatta gttcatagcc catatatgga gttccgcgtt      60
acataactta cggtaaatgg cccgcctggc tgaccgccca acgaccccccg cccattgacg     120 tcaataatga cgtatgttcc catagtaacg ccaatagggg actttccaatg acgtcaatgg     180 gtggagtatt tacggtaaac tgcccacttg gcagtacatc aagtgtatca tatgccaagt     240 acgccccctta ttgacgtcaa tgacggaaaa tggcccgcct ggcattaagc ccagtacatg     300
acctattggg actttcctac ttggcagtac atctacgtat tagtcatcgc tattaccatg     360
gtgatgcggt tttggcagta catcaatggg cgtggatagc ggtttgactc acggggattt     420
```

| | |
|---|---|
| ccaagtctcc accccattga cgtcaatggg agtttgtttt ggcaccaaaa tcaacgggac | 480 |
| tttccaaaat gtcgtaacaa ctccgcccca ttgacgcaaa tgggcggtag gcgtgtacgg | 540 |
| tgggaggtct atataagcag agctggttta gtgaaccgtc agatccgcta gcgctaccgg | 600 |
| tcgccaccat ggtgagcaag ggcgaggagc tgttcaccgg ggtggtgccc atcctggtcg | 660 |
| agctggacgg cgacgtaaac ggccacaagt tcagcgtgtc cggcgagggc gagggcgatg | 720 |
| ccacctacgg caagctgacc ctgaagttca tctgcaccac cggcaagctg cccgtgccct | 780 |
| ggcccaccct cgtgaccacc ctgacctacg gcgtgcagtg cttcagccgc taccccgacc | 840 |
| acatgaagca gcacgacttc ttcaagtccg ccatgcccga aggctacgtc caggagcgca | 900 |
| ccatcttctt caaggacgac ggcaactaca agacccgcgc cgaggtgaag ttcgagggcg | 960 |
| acaccctggt gaaccgcatc gagctgaagg gcatcgactt caaggaggac ggcaacatcc | 1020 |
| tggggcacaa gctggagtac aactacaaca gccacaacgt ctatatcatg gccgacaagc | 1080 |
| agaagaacgg catcaaggtg aacttcaaga tccgccacaa catcgaggac ggcagcgtgc | 1140 |
| agctcgccga ccactaccag cagaacaccc ccatcggcga cggccccgtg ctgctgcccg | 1200 |
| acaaccacta cctgagcacc cagtccgccc tgagcaaaga ccccaacgag aagcgcgatc | 1260 |
| acatggtcct gctggagttc gtgaccgccg ccgggatcac tctcggcatg gacgagctgt | 1320 |
| acaagtccgg actcagatcc accggatcta gataactgat cataatcagc cataccacat | 1380 |
| ttgtagaggt tttacttgct ttaaaaaacc tcccacacct ccccctgaac ctgaaacata | 1440 |
| aaatgaatgc aattgttgtt gttaacttgt ttattgcagc ttataatggt tacaaataaa | 1500 |
| gcaatagcat cacaaatttc acaaataaag catttttttc actgcattct agttgtggtt | 1560 |
| tgtccaaact catcaatgta tcttaacgcg aactacgtca ggtggcactt ttcggggaaa | 1620 |
| tgtgcgcgga acccctattt gtttattttt ctaaatacat tcaaatatgt atccgctcat | 1680 |
| gagacaataa ccctgataaa tgcttcaata atattgaaaa aggaagagta tgagtattca | 1740 |
| acatttccgt gtcgccctta ttcccttttt tgcggcattt tgccttcctg tttttgctca | 1800 |
| cccagaaacg ctggtgaaag taaaagatgc tgaagatcag ttgggtgcac gagtgggtta | 1860 |
| catcgaactg gatctcaaca gcggtaagat ccttgagagt tttcgccccg aagaacgttc | 1920 |
| tccaatgatg agcactttta aagttctgct atgtggcgcg gtattatccc gtgttgacgc | 1980 |
| cgggcaagag caactcggtc gccgcataca ctattctcag aatgacttgg ttgagtactc | 2040 |
| accagtcaca gaaaagcatc ttacggatgg catgacagta agagaattat gcagtgctgc | 2100 |
| cataaccatg agtgataaca ctgcggccaa cttacttctg acaacgatcg gaggaccgaa | 2160 |
| ggagctaacc gcttttttgc acaacatggg ggatcatgta actcgccttg atcgttggga | 2220 |
| accggagctg aatgaagcca taccaaacga cgagcgtgac accacgatgc ctgtagcaat | 2280 |
| ggcaacaacg ttgcgcaaac tattaactgg cgaactactt actctagctt cccggcaaca | 2340 |
| attaatagac tggatggagg cggataaagt tgcaggacca cttctgcgct cggcccttcc | 2400 |
| ggctggctgg tttattgctg ataaatctgg agccggtgag cgtgggtctc gcggtatcat | 2460 |
| tgcagcactg gggccagatg gtaagccctc ccgtatcgta gttatctaca cgacggggag | 2520 |
| tcaggcaact atggatgaac gaaatagaca gatcgctgag ataggtgcct cactgattaa | 2580 |
| gcattggtaa ctgtcagacc aagtttactc atatatactt tagattgatt taccccggtt | 2640 |
| gataatcaga aaagccccaa aacaggaag attgtataag caaatattta aattgtaaac | 2700 |
| gttaataatt tgttaaaatt cgcgttaaat ttttgttaaa tcagctcatt ttttaaccaa | 2760 |
| taggccgaaa tcggcaaaat cccttataaa tcaaaagaat agcccgagat agggttgagt | 2820 |

-continued

```
gttgttccag tttggaacaa gagtccacta ttaaagaacg tggactccaa cgtcaaaggg      2880
cgaaaaaccg tctatcaggg cgatggccca ctacgtgaac catcacccaa atcaagtttt      2940
ttggggtcga ggtgccgtaa agcactaaat cggaacccta aagggagccc ccgatttaga      3000
gcttgacggg gaaagcgaac gtggcgagaa aggaagggaa gaaagcgaaa ggagcgggcg      3060
ctagggcgct ggcaagtgta gcggtcacgc tgcgcgtaac caccacaccc gccgcgctta      3120
atgcgccgct acagggcgcg taaaaggatc taggtgaaga tccttttttga taatctcatg      3180 accaaaatcc cttaacgtga gttttcgttc cactgagcgt cagaccccgt agaaaagatc      3240
aaaggatctt cttgagatcc tttttttctg cgcgtaatct ggtgcttgca acaaaaaaaa      3300
ccaccgctac cagcggtggt ttgtttgccg gatcaagagc taccaactct ttttccgaag      3360
gtaactggct tcagcagagc gcagatacca aatactgttc ttctagtgta gccgtagtta      3420
ggccaccact tcaagaactc tgtagcaccg cctacatacc tcgctctgct aatcctgtta      3480
ccagtggctg ctgccagtgg cgataagtcg tgtcttaccg ggttggactc aagacgatag      3540
ttaccggata aggcgcagcg gtcgggctga acggggggtt cgtgcacaca gcccagcttg      3600
gagcgaacga cctacaccga actgagatac ctacagcgtg agctatgaga aagcgccacg      3660
cttcccgaag ggagaaaggc ggacaggtat ccggtaagcg gcagggtcgg aacaggagag      3720
cgcacgaggg agcttccagg gggaaacgcc tggtatcttt atagtcctgt cgggtttcgc      3780
cacctctgac ttgagcgtcg atttttgtga tgctcgtcag ggggggcggag cctatggaaa      3840 aacgccagca acgcggcctt tttacggttc ctggcctttt gctggccttt tgctcacatg      3900
taatgtgagt tagctcactc attaggcacc ccaggcttta cactttatgc ttccggctcc      3960
tatgttgtgt ggaattgtga gcggataaca atttcacaca ggaaacagct atgaccatga      4020
ttacgccaag ctacgtaata cgactcacta ggcggccgcg tttaaacaat gtgctcctct      4080
ttggcttgct tccgcgggcc aagccagaca agaaccagtt gacgtcaagc ttcccgggac      4140
gcgtgctagc ggcgcgccga attcctgcag gattcgaggg cccctgcagg tcaattctac      4200
cgggtagggg aggcgctttt cccaaggcag tctggagcat gcgctttagc agccccgctg      4260
gcacttggcg ctacacaagt ggcctctggc ctcgcacaca ttccacatcc accggtagcg      4320
ccaaccggct ccgttctttg gtggccccctt cgcgccacct tctactcctc ccctagtcag      4380
gaagttcccc cccgccccgc agctcgcgtc gtgcaggacg tgacaaatgg aagtagcacg      4440
tctcactagt ctcgtgcaga tggacagcac cgctgagcaa tggaagcggg taggcctttg      4500
gggcagcggc caatagcagc tttgctcctt cgctttctgg gctcagaggc tgggaagggg      4560
tgggtccggg ggcgggctca ggggcgggct caggggcggg gcgggcgcga aggtcctccc      4620
gaggcccggc attctcgcac gcttcaaaag cgcacgtctg ccgcgctgtt ctcctcttcc      4680
tcatctccgg gcctttcgac ctgcagccaa tatgggatcg gccattgaac aagatggatt      4740
gcacgcaggt tctccggccg cttgggtgga gaggctattc ggctatgact gggcacaaca      4800
gacaatcggc tgctctgatg ccgccgtgtt ccggctgtca gcgcagggc gcccggttct      4860 ttttgtcaag accgacctgt ccggtgccct gaatgaactg caggacgagg cagcgcggct      4920
atcgtggctg gccacgacgg gcgttccttg cgcagctgtg ctcgacgttg tcactgaagc      4980
gggaagggac tggctgctat tgggcgaagt gccggggcag gatctcctgt catctcacct      5040
tgctcctgcc gagaaagtat ccatcatggc tgatgcaatg cggcggctgc atacgcttga      5100
tccggctacc tgcccattcg accaccaagc gaaacatcgc atcgagcgag cacgtactcg      5160
```

```
gatggaagcc ggtcttgtcg atcaggatga tctggacgaa gagcatcagg ggctcgcgcc    5220
agccgaactg ttcgccaggc tcaaggcgcg catgcccgac ggcgatgatc tcgtcgtgac    5280
ccatggcgat gcctgcttgc cgaatatcat ggtggaaaat ggccgctttt ctggattcat    5340
cgactgtggc cggctgggtg tggcggaccg ctatcaggac atagcgttgg ctacccgtga    5400
tattgctgaa gagcttggcg gcgaatgggc tgaccgcttc ctcgtgcttt acggtatcgc    5460
cgctcccgat tcgcagcgca tcgccttcta tcgccttctt gacgagttct tctgagggga    5520
tcgatccgtc ctgtaagtct gcagaaattg atgatctatt aaacaataaa gatgtccact    5580
aaaatggaag ttttcctgt catactttgt taagaagggt gagaacagag tacctacatt    5640
ttgaatggaa ggattggagc tacggggtg ggggtgggt gggattagat aaatgcctgc    5700
tctttactga aggctcttta ctattgcttt atgataatgt ttcatagttg gatatcataa    5760
tttaaacaag caaaaccaaa ttaagggcca gctcattcct cccactcatg atctatagat    5820
ctatagatct ctcgtgggat cattgttttt ctcttgattc ccactttgtg gttctaagta    5880
ctgtggtttc caaatgtgtc agtttcatag cctgaagaac gagatcagca gcctctgttc    5940
cacatacact tcattctcag tattgttttg ccaagttcta attccatcag aagctgactc    6000
tagatctgga tccggccagc taggccgtcg acctcgagtg atcaggtacc aaggtcctcg    6060
ctctgtgtcc gttgagctcg acgacacagg acacgcaaat taattaaggc cggcccgtac    6120
cctctagtca aggccttaag tgagtcgtat tacggactgg ccgtcgtttt acaacgtcgt    6180
gactgggaaa accctggcgt tacccaactt aatcgccttg cagcacatcc cccttcgcc    6240 agctggcgta atagcgaaga ggcccgcacc gatcgccctt cccaacagtt gcgcagcctg    6300
aatggcgaat ggcgcttcgc ttggtaataa agcccgcttc ggcgggcttt ttttt         6355
```

<210> SEQ ID NO 3
<211> LENGTH: 26
<212> TYPE: DNA
<213> ORGANISM: Artificial Sequence
<220> FEATURE:
<223> OTHER INFORMATION: Phage Vector

<400> SEQUENCE: 3

```
tgtgctcctc tttggcttgc ttccaa                                         26
```

<210> SEQ ID NO 4
<211> LENGTH: 26
<212> TYPE: DNA
<213> ORGANISM: Artificial Sequence
<220> FEATURE:
<223> OTHER INFORMATION: Phage Vector

<400> SEQUENCE: 4

```
ttggaagcaa gccaaagagg agcaca                                         26
```

<210> SEQ ID NO 5
<211> LENGTH: 25
<212> TYPE: DNA
<213> ORGANISM: Artificial Sequence
<220> FEATURE:
<223> OTHER INFORMATION: Phage Vector

<400> SEQUENCE: 5

```
ctggttcttg tctggcttgg cccaa                                          25
```

<210> SEQ ID NO 6
<211> LENGTH: 25

```
<212> TYPE: DNA
<213> ORGANISM: Artificial Sequence
<220> FEATURE:
<223> OTHER INFORMATION: Phage Vector

<400> SEQUENCE: 6
ttgggccaag ccagacaaga accag                                      25

<210> SEQ ID NO 7
<211> LENGTH: 24
<212> TYPE: DNA
<213> ORGANISM: Artificial Sequence
<220> FEATURE:
<223> OTHER INFORMATION: Phage Vector

<400> SEQUENCE: 7
ggtcctcgct ctgtgtccgt tgaa                                       24

<210> SEQ ID NO 8
<211> LENGTH: 24
<212> TYPE: DNA
<213> ORGANISM: Artificial Sequence
<220> FEATURE:
<223> OTHER INFORMATION: Phage Vector

<400> SEQUENCE: 8
ttcaacggac acagagcgag gacc                                       24

<210> SEQ ID NO 9
<211> LENGTH: 23
<212> TYPE: DNA
<213> ORGANISM: Artificial Sequence
<220> FEATURE:
<223> OTHER INFORMATION: Phage Vector

<400> SEQUENCE: 9
tttgcgtgtc ctgtgtcgtc gaa                                        23

<210> SEQ ID NO 10
<211> LENGTH: 23
<212> TYPE: DNA
<213> ORGANISM: Artificial Sequence
<220> FEATURE:
<223> OTHER INFORMATION: Phage Vector

<400> SEQUENCE: 10
ttcgacgaca caggacacgc aaa                                        23

<210> SEQ ID NO 11
<211> LENGTH: 28
<212> TYPE: DNA
<213> ORGANISM: Artificial Sequence
<220> FEATURE:
<223> OTHER INFORMATION: Phage Vector

<400> SEQUENCE: 11
aatgtgctcc tctttggctt gcttccgc                                   28

<210> SEQ ID NO 12
<211> LENGTH: 26
<212> TYPE: DNA
<213> ORGANISM: Artificial Sequence
<220> FEATURE:
<223> OTHER INFORMATION: Phage Vector

<400> SEQUENCE: 12
```

```
ggaagcaagc caaagaggag cacatt                                          26

<210> SEQ ID NO 13
<211> LENGTH: 27
<212> TYPE: DNA
<213> ORGANISM: Artificial Sequence
<220> FEATURE:
<223> OTHER INFORMATION: Phage Vector

<400> SEQUENCE: 13
aactggttct tgtctggctt ggcccgc                                         27

<210> SEQ ID NO 14
<211> LENGTH: 25
<212> TYPE: DNA
<213> ORGANISM: Artificial Sequence
<220> FEATURE:
<223> OTHER INFORMATION: Phage Vector

<400> SEQUENCE: 14
gggccaagcc agacaagaac cagtt                                           25

<210> SEQ ID NO 15
<211> LENGTH: 28
<212> TYPE: DNA
<213> ORGANISM: Artificial Sequence
<220> FEATURE:
<223> OTHER INFORMATION: Phage Vector

<400> SEQUENCE: 15
aaggtcctcg ctctgtgtcc gttgagct                                        28

<210> SEQ ID NO 16
<211> LENGTH: 24
<212> TYPE: DNA
<213> ORGANISM: Artificial Sequence
<220> FEATURE:
<223> OTHER INFORMATION: Phage Vector

<400> SEQUENCE: 16
caacggacac agagcgagga cctt                                            24

<210> SEQ ID NO 17
<211> LENGTH: 27
<212> TYPE: DNA
<213> ORGANISM: Artificial Sequence
<220> FEATURE:
<223> OTHER INFORMATION: Phage Vector

<400> SEQUENCE: 17
aatttgcgtg tcctgtgtcg tcgagct                                         27

<210> SEQ ID NO 18
<211> LENGTH: 23
<212> TYPE: DNA
<213> ORGANISM: Artificial Sequence
<220> FEATURE:
<223> OTHER INFORMATION: Phage Vector

<400> SEQUENCE: 18
cgacgacaca ggacacgcaa att                                             23

<210> SEQ ID NO 19
<211> LENGTH: 1530
<212> TYPE: DNA
<213> ORGANISM: Mus musculus
```

<400> SEQUENCE: 19

```
tcggttgggc ccagcaactt ctagcaagca ggctacccct taggaccatcc atatccgatg      60
agctctacag tggctgcctc cactatgcct gtgtctgtgg cggcctccaa gaaggagtct     120
ccaggtagat ggggccttgg agaggatcca acaggtgtgg gcccctcgct ccagtgccga     180
gtgtgtgggg acagcagcag tgggaaacat tatggcatct atgcctgcaa tggctgcagt     240
ggcttcttca agaggagtgt gagaaggagg ctcatctaca ggtgccaagt cggggcaggg     300
atgtgcccag tggataaggc ccatcgcaat cagtgccagg cctgccggct gaagaagtgc     360
ttacaagcag gcatgaacca agatgctgtg cagaatgagc gccaacctcg gagcatggct     420
caggtccacc tggatgccat ggaaacaggc agtgaccccc gatcagaacc agtggtagcc     480
tctcctgctc tggcagggcc cagtccccgg ggccccacgt ctgtgtctgc aaccagagcc     540
atgggccacc actttatggc cagccttatc accgccgaaa cttgtgctaa actggagcca     600
gaggacgctg aagagaatat tgatgtcacc agcaatgacc ccgagttccc cgcatccccc     660
tgcagtctgg atggcatcca tgagacatct gctcgcctgc tcttcatggc tgtcaaatgg     720
gccaaaaact tgcctgtgtt ttccaacctg ccttttccggg accaggtgat cttgctggaa     780
gaggcatgga atgagctttt ccttcttgga gccatacagt ggtctctgcc cctggacagc     840
tgcccactgc tggcaccacc tgaggcgtcc ggcagctctc agggcaggct ggccttggcc     900
agtgcagaga cgcgcttcct gcaggaaacc atctcccggt tccgagctct ggcagtggat     960
cccacagagt ttgcctgcct gaaggccctg gtcctcttca aacctgaaac acgaggcctg    1020
aaggatcctg agcacgtgga ggctttgcag gaccagtccc aggtgatgct aagccagcat    1080
agcaaggctc accacccccag ccagcctgtg aggtttggga aattgctcct cctgctccca    1140
tctttgaggt tcctcacggc tgagcgcatt gagcttctct tcttcagaaa gaccataggg    1200
aacactccga tggagaagct cctgtgtgac atgttcaaaa actagttggg agtgccaagt    1260
gtccacaggc acccaggggg gcagcacatc ttagaagcta aatagttccc tgcctttctc    1320
agccagtaat tccacattca ggtattccta cctagcagaa atttctccca aaatatatta    1380
ttggcatatt cattgccatc ctaatcttaa taccctaac tctgcttggg cagtagaatg    1440
catggatgcg ttgttatatt cataggagaa acagctttgg caaaaaaaaa aaaaaaaaa    1500
aaaaaaaaaa aaaaaaaaaa aaaaaaaaaa                                    1530
```

<210> SEQ ID NO 20
<211> LENGTH: 200
<212> TYPE: DNA
<213> ORGANISM: Artificial Sequence
<220> FEATURE:
<223> OTHER INFORMATION: Targeting vector

<400> SEQUENCE: 20

```
agactgaaag acagacagac agacagacag gggttaaaga tggatgcatc ggttgggccc      60
agcaacttct agcaagcagg ctacccttag gaccatccat atccgatgag ctctacagtg     120
gctgcctcca ctatgcctgt gtctgtggcg gcctccaaga aggagtctcc aggtagatgg     180
ggccttggag aggatccaac                                                 200
```

<210> SEQ ID NO 21
<211> LENGTH: 200
<212> TYPE: DNA
<213> ORGANISM: Artificial Sequence
<220> FEATURE:

-continued

```
<223> OTHER INFORMATION: Targeting vector

<400> SEQUENCE: 21
ctccagtgcc gagtgtttgg ggacagcagc agtgggaaac attatggcat ctatgcctgc   60
aatggctgca gtggcttctt caagaggagt gtgagaagga ggctcatcta caggtgccac  120
agctctgccg gcctgccccg gtgtgcctag cacgggtgga gggcgttcag ggaaagcgga  180
agacgagacc agggcaaaca                                              200
```